(12) United States Patent
Wu

(10) Patent No.: US 10,150,104 B2
(45) Date of Patent: Dec. 11, 2018

(54) METHOD FOR PREPARING AROMATIZATION CATALYSTS

(71) Applicant: Chevron Phillips Chemical Company LP, The Woodlands, TX (US)

(72) Inventor: An-Hsiang Wu, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 342 days.

(21) Appl. No.: 14/935,982

(22) Filed: Nov. 9, 2015

(65) Prior Publication Data

US 2017/0128920 A1 May 11, 2017

(51) Int. Cl.
| | |
|---|---|
| *B01J 29/06* | (2006.01) |
| *B01J 29/62* | (2006.01) |
| *B01J 37/02* | (2006.01) |
| *B01J 37/24* | (2006.01) |
| *B01J 37/26* | (2006.01) |
| *C07C 5/31* | (2006.01) |
| *B01J 37/22* | (2006.01) |
| *B01J 29/60* | (2006.01) |
| *C07C 5/41* | (2006.01) |

(52) U.S. Cl.
CPC ........... *B01J 29/62* (2013.01); *B01J 29/60* (2013.01); *B01J 37/0201* (2013.01); *B01J 37/0203* (2013.01); *B01J 37/0205* (2013.01); *B01J 37/22* (2013.01); *B01J 37/24* (2013.01); *B01J 37/26* (2013.01); *C07C 5/31* (2013.01); *C07C 5/417* (2013.01); *B01J 2229/186* (2013.01); *C07C 2521/02* (2013.01); *C07C 2529/62* (2013.01)

(58) Field of Classification Search
CPC .. B01J 29/60; B01J 2229/186; B01J 37/0201; B01J 37/0205; B01J 37/0203; B01J 37/22; B01J 37/24; B01J 37/26; C07C 2529/62; C07C 2521/02
USPC .................... 502/60, 74, 224, 229, 207, 230
See application file for complete search history.

(56) References Cited

U.S. PATENT DOCUMENTS

| | | | | |
|---|---|---|---|---|
| 4,897,177 A | * | 1/1990 | Nadler ................. | C10G 35/095 208/135 |
| 5,558,851 A | | 9/1996 | Miller | |
| 5,883,031 A | | 3/1999 | Innes et al. | |
| 5,968,343 A | * | 10/1999 | Drake ..................... | B01J 29/40 208/114 |
| 5,997,730 A | | 12/1999 | Drake et al. | |
| 6,066,251 A | * | 5/2000 | Chen ........................ | B01J 21/02 208/135 |
| 6,077,984 A | | 6/2000 | Drake et al. | |
| 6,080,901 A | | 6/2000 | Drake et al. | |
| 6,107,534 A | | 8/2000 | Drake et al. | |
| 6,156,689 A | * | 12/2000 | Kimble .................... | B01J 29/40 502/202 |
| 6,160,191 A | * | 12/2000 | Smith ..................... | C01B 39/02 208/109 |
| 6,190,539 B1 | | 2/2001 | Holtermann et al. | |
| 6,207,042 B1 | | 3/2001 | Holtermann et al. | |
| 6,562,752 B2 | * | 5/2003 | Kasztelan ................ | B01J 27/04 502/202 |
| 7,153,801 B2 | | 12/2006 | Wu | |
| 7,902,105 B2 | | 3/2011 | Khare | |
| 8,263,518 B2 | | 9/2012 | Khare | |
| 8,461,404 B2 | | 6/2013 | Khare | |
| 2002/0045539 A1 | * | 4/2002 | Kasztelan ................ | B01J 27/04 502/222 |
| 2002/0120169 A1 | * | 8/2002 | Spagnol ................... | B01J 29/90 568/316 |
| 2005/0115872 A1 | * | 6/2005 | Thomazeau ............. | B01J 23/30 208/216 R |
| 2009/0156871 A1 | * | 6/2009 | Khare .................... | B01J 29/061 585/408 |
| 2010/0160150 A1 | | 6/2010 | Wu | |
| 2010/0160702 A1 | | 6/2010 | Wu | |
| 2013/0035530 A1 | * | 2/2013 | Khare .................... | B01J 29/061 585/419 |
| 2013/0231511 A1 | * | 9/2013 | Wu .......................... | B01J 38/46 585/407 |

OTHER PUBLICATIONS

"Group notation revised in periodic table," Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
UOP Method 578-02, "Automated Pore Volume and Pore Size Distribution of Porous Substances by Mercury Porosimetry," UOP LLC, 1984, pp. 1-14.

* cited by examiner

*Primary Examiner* — Elizabeth D Wood
(74) *Attorney, Agent, or Firm* — Conley Rose, P.C.; Rodney B. Carroll; Monte R. Rhodes

(57) ABSTRACT

A method of preparing an aromatization catalyst comprising contacting a zeolitic support with a metal-containing compound and a boron-containing compound to produce an impregnated support, and contacting the impregnated support with an activating composition to produce an aromatization catalyst, wherein the activating composition comprises a chlorine-containing compound and a fluorine-containing compound, and wherein the impregnated support is heated in the presence of the activating composition to a temperature in the range of from about 100° C. to about 500° C.

20 Claims, 3 Drawing Sheets

METHOD FOR PREPARING AROMATIZATION CATALYSTS

TECHNICAL FIELD

The present disclosure relates to an aromatization catalyst and methods of making and using the aromatization catalyst for the aromatization of a hydrocarbon feed to aromatic compounds. More specifically, the present disclosure relates to an aromatization catalyst comprising boron and methods of making and using the same.

BACKGROUND

The catalytic conversion of a hydrocarbon feed into aromatic compounds, referred to as aromatization, is an important industrial process used to produce fundamental building block chemicals on which a large portion of the chemical industry is based. The aromatization reactions can include the dehydrogenation, isomerization, and hydrocracking of hydrocarbons, each of which produces certain aromatic compounds. These reactions are generally conducted in one or more aromatization reactors containing aromatization catalysts. These aromatization catalysts have increased conversion rates for the reaction, increased selectivity to the desired aromatic compounds, or both. However, one pitfall of aromatization catalysts is the occurrence of cracking reactions concurrently with aromatization reactions. While under commercial aromatization conditions, the aromatization catalysts slowly lose activity as evidenced by a reduction in conversion rates and an increase in reactor temperature required to maintain conversion. The increased reactor temperature combined with the aging of the catalyst can lead to an increase in cracking reactions as the aromatization catalyst ages. The increase in cracking reactions can be measured as a loss of selectivity to desired products. Because cracking reactions downgrade a valuable hydrocarbon feed priced according to unleaded gasoline benchmarks to lower value products priced according to fuel value, an increase in cracking reactions, particularly when approaching end-of-run, has a significant impact on the economics of aromatization. Thus, there is an ongoing need to improve aromatization catalysts.

BRIEF SUMMARY

Disclosed herein is a method of preparing an aromatization catalyst comprising contacting a zeolitic support with a metal-containing compound and a boron-containing compound to produce an impregnated support, and contacting the impregnated support with an activating composition to produce an aromatization catalyst, wherein the activating composition comprises a chlorine-containing compound and a fluorine-containing compound, and wherein the impregnated support is heated in the presence of the activating composition to a temperature in the range of from about 100° C. to about 500° C.

Also disclosed herein is a method of preparing an aromatization catalyst comprising contacting a zeolitic support with an impregnating composition comprising a platinum-containing compound and a boron-containing compound to produce a platinum-boron containing zeolitic support, and contacting the platinum-boron containing zeolitic support with an activating composition comprising a chlorine-containing compound and a fluorine-containing compound to produce an aromatization catalyst, wherein the platinum-boron containing zeolitic support is heated in the presence of the activating composition to a temperature in the range of from about 100° C. to about 500° C.

Further disclosed herein is a catalyst composition comprising a zeolitic support, chlorine, fluorine, platinum and non-framework boron; wherein the zeolitic support further comprises an L-zeolite.

BRIEF DESCRIPTION OF THE DRAWINGS

The following figures form part of the present specification and are included to further demonstrate certain aspects of the present inventions. The invention may be better understood by reference to one or more of these figures in combination with the detailed description of specific embodiments presented herein.

DETAILED DESCRIPTION

Figure 1:
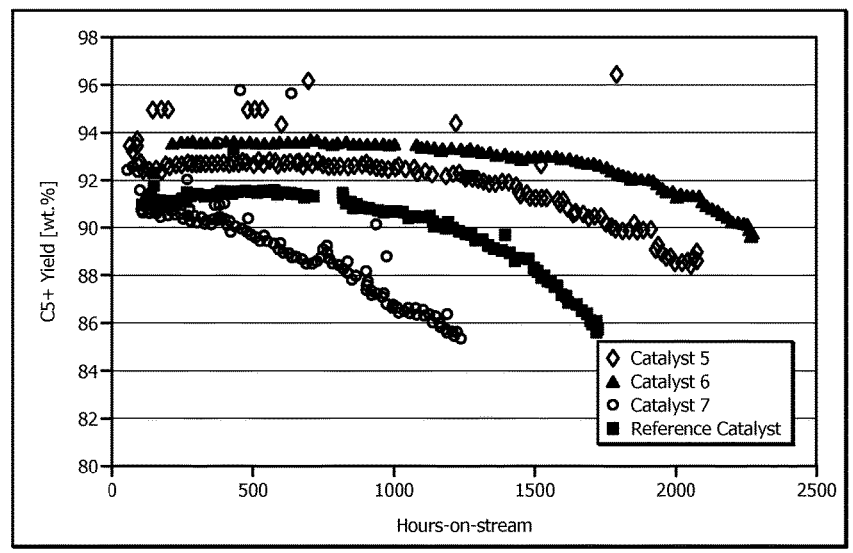
FIG. 1 illustrates a comparison of C5+ yield over time for aromatization catalysts with different amounts of boron.

It should be understood at the outset that although an illustrative implementation of one or more embodiments are provided below, the disclosed systems and methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are methods of making aromatization catalysts. In an embodiment, a method of preparing an aromatization catalyst can generally comprise the steps of (a) contacting a zeolitic support with a metal-containing compound and a boron-containing compound to produce an impregnated support; and (b) contacting the impregnated support with an activating composition to produce an aromatization catalyst, wherein the activating composition can comprise a chlorine-containing compound, a fluorine-containing compound, or both a chlorine-containing compound and a fluorine-containing compound, and wherein the impregnated support is heated in the presence of the activating composition to a temperature in the range of from about 100° C. to about 500° C. In an embodiment, the impregnated support, the aromatization catalyst, or both the impregnated support and the aromatization catalyst can contain non-framework boron. In an embodiment, the aromatization catalyst can be used to convert a hydrocarbon feed into aromatic compounds. Generally, these conversions of a hydrocarbon feed into aromatic compounds are carried out in one or more aromatization reactors. In an embodiment, the aromatization catalysts of the type disclosed herein can display a catalytic selectivity that remains stable over time.

In an embodiment, a method of the present disclosure can comprise preparing an aromatization catalyst comprising a zeolitic support, one or more catalytically active metals, one or more halides, and boron. While the present disclosure will be discussed in detail in the context of a method for producing such an aromatization catalyst, it should be understood that such method or any steps thereof can be applied in a method for producing any other suitable catalyst. The aromatization catalyst can comprise any catalyst compatible with the disclosed methods and materials.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogen atoms, as necessary for the situation, removed from the alkane. Throughout, the disclosure that a substituent or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "hydrocarbon" whenever used in this specification and claims refers to a compound containing only carbon and hydrogen, and can be linear or branched unless otherwise specified. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups; additionally, the "hydrocarbyl group," "hydrocarbylene group," and "hydrocarbon group" groups can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

The term "alkane" whenever used in this specification and claims refers to a saturated hydrocarbon compound, for example hexane. Other identifiers can be utilized to indicate the presence of particular groups in the alkane (e.g. halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups; additionally, the "alkyl group," "alkylene group," and "alkane group" can be linear or branched unless otherwise specified.

A "cycloalkane" is a saturated cyclic hydrocarbon, with or without side chains, for example cyclohexane. Other identifiers can be utilized to indicate the presence of particular groups in the cycloalkane (e.g., halogenated cycloalkane indicates the presence of one or more halogen atoms replacing an equivalent number of hydrogen atoms in the cycloalkane). Unsaturated cyclic hydrocarbons having one or more endocyclic double or triple bonds are called cycloalkenes and cycloalkynes, respectively. Cycloalkenes and cycloalkynes having only one, only two, and only three endocyclic double or triple bonds, respectively, can be identified by use of the term "mono," "di," and "tri within the name of the cycloalkene or cycloalkyne. Cycloalkenes and cycloalkynes can further identify the position of the endocyclic double or triple bonds.

The term "hydrocarbon feed" whenever used in this specification and claims refers to a mixture of hydrocarbons. In an embodiment, the hydrocarbon feed can comprise non-aromatic hydrocarbons including linear or branched alkanes, cycloalkanes, or alkenes containing at least six carbon atoms. The feed (e.g., hydrocarbon feed) to the aromatization system can be a mixture of hydrocarbons comprising $C_6$ to $C_8$ hydrocarbons containing up to about 10 wt. %, or alternatively up to about 15 wt. % of $C_5$ and lighter hydrocarbons (C5−) and containing up to about 10 wt. % of $C_9$ and heavier hydrocarbons (C9+). Such low levels of C9+ and C5-hydrocarbons can maximize the yield of high value aromatics. In some embodiments, an optimal hydrocarbon feed can maximize the percentage of $C_6$ hydrocarbons. Such a feed can be achieved by separating a hydrocarbon feed such as a full range naphtha into a light hydrocarbon feed fraction and a heavy hydrocarbon feed fraction, and using the light hydrocarbon feed fraction. In another embodiment, the hydrocarbon feed can comprise a naphtha feed. The naphtha feed can be a hydrocarbon feed with a boiling range of from about 70° F. (21.1° C.) to about 450° F. (232.2° C.). The naphtha feed could contain aliphatic, naphthenic, or paraffinic hydrocarbons.

Figure 3:
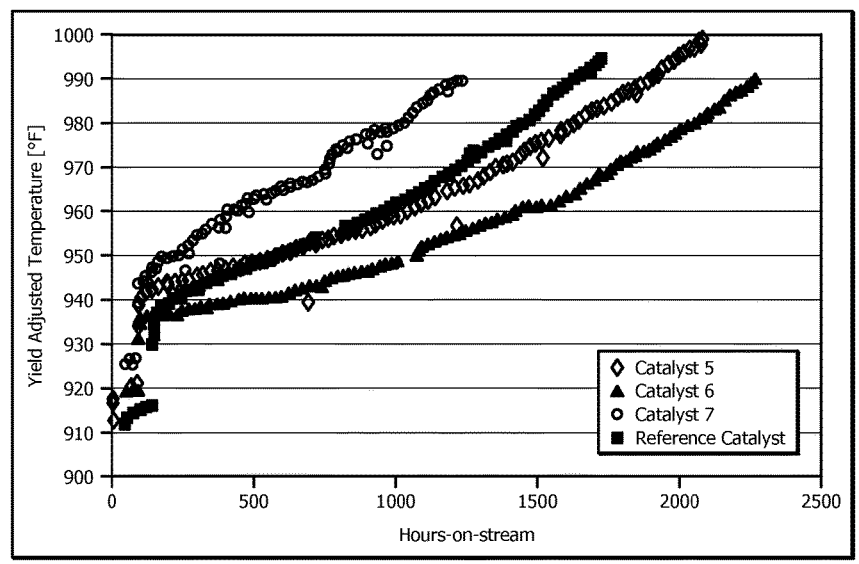
FIG. 3 illustrates a comparison of fouling curves for aromatization catalysts with different amounts of boron.
Figure 4A:
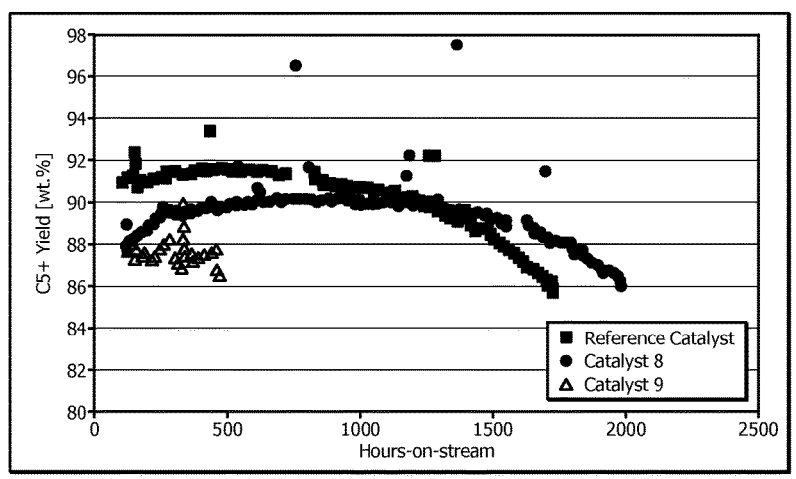
FIG. 4A illustrates a comparison of C5+ yield over time for various aromatization catalysts.
Figure 4B:
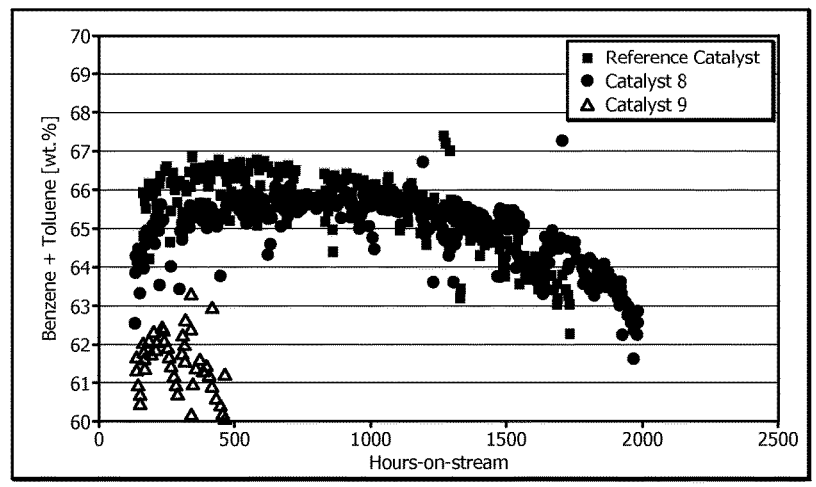
FIG. 4B illustrates a comparison of the amount of benzene and toluene produced over time by various aromatization catalysts.
Figure 4C:
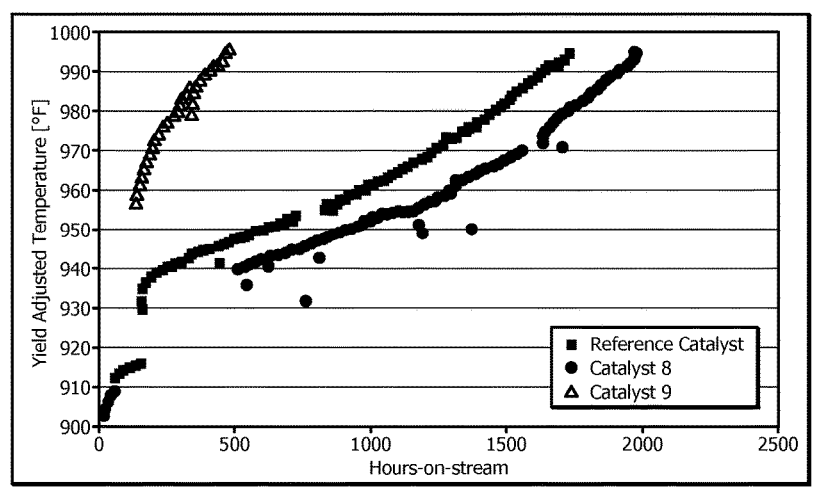
FIG. 4C illustrates a comparison of fouling curves for various aromatization catalysts.

A catalyst fouling curve may be used to characterize the deactivation of a catalyst. Referring to FIG. 3 and FIG. 4C, a catalyst-fouling curve is obtained by plotting the yield-adjusted temperature of the catalyst as a function of time. The slope of the plot is positive and represents increases in the reactor and catalyst temperature necessary to maintain a constant product yield. As will be understood by one of ordinary skill in the art, the specific definition of yield-adjusted temperature will depend on a variety of reaction conditions, such as for example the number of reactors employed in a given system and the specific target yield chosen. In an embodiment, the yield-adjusted temperature may be the temperature of an isothermal or adiabatic catalyst bed. Alternatively, the yield-adjusted temperature may be the catalyst temperature normalized to a specific level of catalyst productivity at a defined set of process conditions. Alternatively, the yield-adjusted temperature for an aromatization process may be the isothermal furnace set point temperature, corrected to a specific target yield of % aromatics in an overall product stream. This furnace set point temperature is normally the same as the bed inlet temperature. Alternatively, the yield-adjusted temperature for an adiabatic aromatization process may be the reactor inlet set point temperature, corrected for differences from a specific target yield of % aromatics in the overall product stream.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. The term "consisting essentially of" occupies a middle ground between closed terms like "consisting of" and fully open terms like "comprising." Absent an indication to the contrary, when describing a compound or composition "consisting essentially of" is not to be construed as "comprising," but is intended to describe the recited component that includes materials that do not significantly alter the composition or method to which the term is applied. For example, a hydrocarbon feed consisting essentially of a material A can include impurities typically present in a commercially produced or commercially available sample of the recited compound or composition. When a claim includes different features, feature classes, or both (for example, a method step, hydrocarbon feed features, product features, among other possibilities), the transitional terms comprising, consisting essentially of, and consisting of apply only to feature class to which is utilized and it is possible to have different transitional terms or phrases utilized with different features within a claim. For example a method can comprise several recited steps (and other non-recited steps) but utilize an aromatization catalyst system preparation consisting of specific or alternatively consisting essentially of specific steps but utilize a catalyst system comprising recited components and other non-recited components.

While compositions and methods are described in terms of "comprising" (or another broad term) various components, steps, compositions, methods, or combinations thereof can also be described using narrower terms such as "consist essentially of" or "consist of" the various components, steps, compositions, methods, or combinations thereof.

Use of the term "optionally" with respect to any element of a claim is intended to mean that the subject element is required, or alternatively, is not required. Both alternatives are intended to be within the scope of the claim.

The terms "a," "an," and "the" are intended, unless specifically indicated otherwise, to include plural alternatives, e.g., at least one. For any particular compound or group disclosed herein, any name or structure presented is intended to encompass all conformational isomers, regioisomers, and stereoisomers that can arise from a particular set of substituents, unless otherwise specified. For example, a general reference to hexane includes n-hexane, 2-methyl-pentane, 3-methyl-pentane, 2,2-dimethylbutane, 2,3-dimethylbutane and a general reference to a butyl group includes an n-butyl group, a sec-butyl group, an iso-butyl group, and t-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum values can be alternatively stated as "at least" or "greater than or equal to" any recited minimum value for the feature disclosed herein. Features within this disclosure that are provided as a maximum values can be alternatively stated as "less than or equal to" any recited maximum value for the feature disclosed herein.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

In an embodiment, the aromatization catalysts disclosed herein can comprise a zeolitic support, one or more catalytically active metals, one or more halides, and boron.

In an embodiment, a support (e.g., zeolitic support) can comprise crystalline aluminosilicates. These crystalline aluminosilicates can include bound medium, large pore zeolites, or mixtures thereof. As used herein, the term "zeolitic support" is used to describe a support comprising crystalline aluminosilicates. For purposes of the disclosure herein, the terms "support" and "zeolitic support" can be used interchangeably. In an embodiment, the support can further comprise a binding agent or binder, such as for example silica, alumina, clays, titania, magnesium oxide, and the like, or combinations thereof.

Zeolites, both natural and synthetic, are known to have catalytic properties for many hydrocarbon processes. The term "zeolite" generally refers to a particular group of hydrated, crystalline aluminosilicates. Zeolites typically are ordered porous crystalline aluminosilicates having a structure with cavities and channels interconnected by channels. The cavities and channels throughout the crystalline material generally can be of a size to allow selective separation and reaction of hydrocarbons. Generally, zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically is balanced by the inclusion of cations within a crystal structure of the aluminosilicates, such as for example metals, alkali metals, alkaline earth metals, or hydrogen.

In an embodiment, the zeolitic support can comprise a medium or large pore zeolite. Nonlimiting examples of large pore zeolites suitable for use in the present disclosure include L-zeolite, Y-zeolite, mordenite, omega zeolite, beta zeolite, or other types of zeolites.

In an embodiment, the zeolitic support can comprise an L-zeolite, also referred to as LTL zeolite. L zeolitic supports are a sub-group of zeolitic supports. Typical L-zeolites contain mole ratios of oxides in accordance with the following formula:

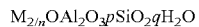

$$M_{2/n}O\cdot Al_2O_3\cdot pSiO_2\cdot qH_2O$$

wherein "M" designates at least one exchangeable cation such as barium, calcium, cerium, lithium, magnesium, potassium, sodium, strontium, zinc, or combinations thereof, as well as non-metallic cations like hydronium and ammonium ions, which can be replaced by other exchangeable cations without causing a substantial alteration of the basic crystal structure of the L-zeolite. The "n" in the formula represents the valence of "M", "p" is 2 or greater; and "q" is the number of water molecules contained in the channels or interconnected voids with the zeolite.

In an embodiment, the zeolitic support can comprise a bound potassium L-zeolite, also referred to as KL zeolite. The term "KL zeolite" as used herein refers to L-zeolites in which the principal cation M incorporated in the zeolite is potassium. In some embodiments, the zeolitic support can comprise a KL zeolite. In other embodiments, the zeolitic support can comprise a mixture of a zeolite and a binding agent.

In an embodiment, the zeolitic support can comprise up to about 95 wt. % L-zeolite, alternatively from about 60 wt. % to about 95 wt. % L-zeolite, alternatively from about 70 wt. % to about 92 wt. % L-zeolite, or alternatively from about 80 wt. % to about 90 wt. % L-zeolite, based on the total weight of the zeolitic support.

In an embodiment, the zeolitic support of the type disclosed herein can have a relatively high surface area, such as for example a surface area of equal to or greater than about 165 square meters per gram (m²/g), alternatively greater than about 170 m²/g, alternatively greater than about 175 m²/g, or alternatively greater than about 180 m²/g. In some embodiments, the zeolitic support can have a surface area of from about 165 m²/g to about 250 m²/g, alternatively from about 165 m²/g to about 225 m²/g, alternatively from about 170 m²/g to about 220 m²/g, alternatively from about 170 m²/g to about 210 m²/g, alternatively from about 175 m²/g to about 225 m²/g, alternatively from about 175 m²/g to about 210 m²/g, alternatively from about 180 m²/g to about 220 m²/g, or alternatively from about 180 m²/g to about 200 m²/g. As will be appreciated by one of skill in the art, and with the help of this disclosure, a zeolitic support with any suitable surface area could be used for the aromatization catalysts of the type disclosed herein. An example of a suitable method for determining the surface area of supports includes the Brunauer, Emmett, and Teller ("BET") method, which measures the quantity of nitrogen adsorbed on the support.

In an embodiment, the zeolitic support of the type disclosed herein can be further characterized by relatively high total pore volumes, such as for example a total pore volume of equal to or greater than about 0.17 cc/g, alternatively greater than about 0.175 cc/g, alternatively greater than about 0.18 cc/g, alternatively greater than about 0.185 cc/g, alternatively from about 0.17 cc/g to about 0.25 cc/g, alternatively from about 0.17 cc/g to about 0.24 cc/g, alternatively from about 0.175 cc/g to about 0.24 cc/g, alternatively from about 0.18 cc/g to about 0.24 cc/g, or alternatively from about 0.17 cc/g to about 0.23 cc/g. In such embodiment, the total pore volume can encompass pore diameters of up to and including about 2000 Å.

In an embodiment, the zeolitic support of the type disclosed herein can be further characterized by a micropore volume of equal to or greater than about 0.045 cc/g, alternatively greater than about 0.05 cc/g, alternatively greater than about 0.055 cc/g, alternatively greater than about 0.06 cc/g, alternatively from about 0.045 cc/g to about 0.09 cc/g, alternatively from about 0.05 cc/g to about 0.09 cc/g, alternatively from about 0.055 cc/g to about 0.085 cc/g, alternatively from about 0.06 cc/g to about 0.09 cc/g, alternatively from about 0.05 cc/g to about 0.08 cc/g, or alternatively from about 0.055 cc/g to about 0.08 cc/g. In such embodiment, the micropore volume can encompass pore diameters of less than about 20 Å.

The pore volume, the total pore volume, the micropore volume, etc. of supports can be measured by a differential mercury intrusion method such as is described in ASTM UOP578-02, entitled "Automated Pore Volume and Pore Size Distribution of Porous Substances by Mercury Porosimetry," which is incorporated herein by reference in its entirety.

In an embodiment, the aromatization catalyst can comprise one or more catalytically active metals. Herein the disclosure can refer to a metal and a catalytically active metal. In the various embodiments disclosed herein, it is to be expressly understood that the terms "metal" and "catalytically active metal" are used interchangeably and are meant to refer to a metal that catalyzes an aromatization reaction as part of the aromatization catalyst. Groups of elements of the periodic table are indicated using the numbering scheme indicated in the version of the periodic table of elements published in *Chemical and Engineering News*, 63(5), 27, 1985, unless otherwise stated. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements. Nonlimiting examples of metals suitable for use in the present disclosure include Group 8, Group 9, and Group 10 transition metals. In an embodiment, the metals can comprise iron, cobalt, nickel, ruthenium, rhodium, palladium, osmium, iridium, platinum, or combinations thereof. In an embodiment, the metal can comprise a Group 8 transition metal. In an embodiment, the metal can comprise platinum (Pt).

In an embodiment, the metal (e.g., catalytically active metal) can be present in the aromatization catalyst in an amount of from about 0.01 wt. % to about 50 wt. %, alternatively from about 0.1 wt. % to about 50 wt. %, alternatively from about 0.05 wt. % to about 10 wt. %, alternatively from about 0.1 wt. % to about 5 wt. %, alternatively from about 0.2 wt. % to about 3 wt. %, or alternatively from about 0.3 wt. % to about 2 wt. %, based on the total weight of the aromatization catalyst.

In an embodiment, the aromatization catalyst can comprise one or more halides. Nonlimiting examples of halides suitable for use in the present disclosure include chloride, fluoride, bromide, iodide, or combinations thereof.

In an embodiment, the aromatization catalyst can comprise chloride. In an embodiment, chloride can be present in the aromatization catalyst in an amount of from about 0.1 wt. % to about 5 wt. %, alternatively from about 0.2 wt. % to about 3 wt. %, or alternatively from about 0.3 wt. % to about 2 wt. %, based on the total weight of the aromatization catalyst.

In various embodiments, the aromatization catalyst can comprise platinum, and chloride (Cl) in an atomic ratio of Pt:Cl of from about 1.0:0.1 to about 1.0:10, alternatively from about 1.0:0.2 to about 1.0:5.0, or alternatively from about 1.0:0.3 to about 1.0:3.0.

In an embodiment, the aromatization catalyst can comprise fluoride. In an embodiment, fluoride can be present in the aromatization catalyst in an amount of from about 0.1 wt. % to about 10 wt. %, alternatively from about 0.2 wt. % to about 5 wt. %, or alternatively from about 0.3 wt. % to about 3 wt. %, based on the total weight of the aromatization catalyst.

In various embodiments, the aromatization catalyst can comprise platinum, and fluoride (F) in an atomic ratio of Pt:F of from about 1.0:0.1 to about 1.0:10, alternatively from about 1.0:0.2 to about 1.0:5.0, or alternatively from about 1.0:0.3 to about 1.0:3.0.

In an embodiment, the aromatization catalyst can comprise boron. In such embodiment, the boron can be non-framework boron. For purposes of the disclosure herein, "non-framework" boron refers to boron atoms that are not part of a three-dimensional framework of the aluminosilicate. Without wishing to be limited by theory, it is believed that non-framework boron does not participate in the crystal structure of the zeolite. Further, for purposes of the disclosure herein, "framework" boron refers to boron atoms that participate in the crystal structure of the zeolitic support, such as for example boron atoms that replace framework aluminum atoms in the crystal structure of the zeolitic support. As will be appreciated by one of skill in the art, and with the help of this disclosure, framework boron will display specific chemical shifts when the aluminosilicate, the zeolitic support, the impregnated support, or the aromatization catalyst is analyzed by solid-state $^{11}$B magic-angle spinning (MAS) nuclear magnetic resonance (NMR) spectroscopy. In an embodiment, non-framework boron does not display solid-state $^{11}$B MAS NMR chemical shifts associated with framework boron. In an embodiment the aluminosilicate, the zeolitic support, the impregnated support, or the aromatization catalyst contains less than about 10%, alternatively less than about 5%, alternatively less than about 0.1%, or alternatively less than about 0.5% integrated area for chemical shifts associated with framework boron as determined by solid state $^{11}$B MAS NMR analysis, based the total $^{11}$B integrated area.

In an embodiment, boron can be present in the aromatization catalyst in an amount of from about 0.05 wt. % to about 0.9 wt. %, alternatively from about 0.1 wt. % to about 0.7 wt. %, or alternatively from about 0.2 wt. % to about 0.5 wt. %, based on the total weight of the aromatization catalyst.

In various embodiments, the aromatization catalyst can comprise a metal (e.g., a catalytically active metal, platinum, etc.) and boron in a boron:metal atomic ratio of from about 0.5:1 to about 20:1, alternatively from about 0.5:1 to about 10:1, alternatively from about 0.5:1 to about 5:1, alternatively from about 0.5:1 to about 3:1, alternatively from about 0.5:1 to about 2:1, or alternatively from about 0.5:1 to about 1:1.

In an embodiment, the aromatization catalyst can further comprise a rare earth element. Nonlimiting examples of rare earth elements suitable for use in the aromatization catalyst of the present disclosure include lanthanides, praseodymium (Pr), neodymium (Nd), samarium (Sm), europium (Eu), gadolinium (Gd), terbium (Tb), dysprosium (Dy), holmium (Ho), erbium (Er), thulium (Tm), and the like, or combinations thereof. In an embodiment, the aromatization catalyst can comprise thulium.

In an embodiment, the rare earth elements can be present in the aromatization catalyst in an amount of from about 0.1 wt. % to about 5 wt. %, alternatively from about 0.2 wt. % to about 3 wt. %, or alternatively from about 0.3 wt. % to about 2 wt. %, based on the total weight of the aromatization catalyst.

In various embodiments, the aromatization catalyst can comprise a metal (e.g., a catalytically active metal, platinum, etc.) and a rare earth element (e.g., thulium) in a rare earth element:metal atomic ratio of from about 0.5:1 to about 20:1, alternatively from about 0.5:1 to about 10:1, alternatively from about 0.5:1 to about 5:1, alternatively from about 0.5:1 to about 3:1, alternatively from about 0.5:1 to about 2:1, or alternatively from about 0.5:1 to about 1:1.

In an embodiment, the aromatization catalyst can be prepared by using any suitable methodology. In an embodiment, a method of preparing an aromatization catalyst can comprise the steps of contacting a zeolitic support with a metal-containing compound and a boron-containing compound; contacting an impregnated support with an activating composition; and thermally treating the support.

In an embodiment, a zeolitic support of the type disclosed herein can be formed from a support mixture comprising an oxide of a metal or metalloid (e.g., a binder or binding agent), an aluminosilicate and water which can be contacted, for example to form an extrudate. Hereafter, a shaped support mixture exiting a die, with any composition or any form, can be referred to as the extruded support.

In an embodiment, the support mixture can be formed into any suitable shape. In an embodiment, the support mixture can be formed in a shape desired for a final product (e.g., aromatization catalyst). Such shapes include for example, extrudates, cylinders, spheres, granules, agglomerates, pellets, prills, and the like, or combinations thereof. Methods for shaping particles include, for example, extrusion, spray drying, pelletizing, agglomeration, oil drop, and the like. In an embodiment, the support mixture can be formed into an extrudate, for example as described in U.S. Pat. Nos. 5,558,851; 6,190,539; 6,207,042; 7,902,105; 8,263,518; and 8,461,404; each of which is incorporated by reference herein in its entirety.

In an embodiment, the support mixture can further comprise an extrusion aid. Forming pellets or extrudates from zeolites generally involves using various additives, such as for example extrusion aids and viscosity modifiers in addition to binders. These additives are typically organic compounds such as cellulose based materials (e.g., METHOCEL cellulose ethers), ethylene glycol, stearic acid, and the like, or combinations thereof. METHOCEL cellulose ethers are water-soluble methylcellulose and hydroxypropyl methylcellulose polymers; and are commercially available from Dow Chemical Co. Additives for forming extrudates are known to one of ordinary skill in the art. As will be appreciated by one of skill in the art, and with the help of this disclosure, the additives for forming extrudates should not leave a detrimental residue; that is a residue that has undesirable reactivity, a residue that can block pores, or both, after calcination. Washing the extrudates can remove low levels of residues. In an embodiment, additives for forming extrudates suitable for use in the present disclosure do not add significant amounts of alkali or alkaline earth ash to the zeolitic support or aromatization catalyst. In an embodiment, the residue from the extrusion aid can be present in the extrudate in an amount of less than about 0.5 wt. %, alternatively less than about 0.4 wt. %, alternatively less than about 0.3 wt. %, alternatively less than about 0.2 wt. %, or alternatively less than about 0.1 wt. %, based on the total weight of the extrudate.

In an embodiment, the support (e.g., extruded support, extruded zeolitic support, zeolitic support) can be further dried to remove excess liquid (e.g., water), thereby forming a dried support (e.g., dried extruded support, dried extruded zeolitic support, dried zeolitic support). Any suitable conventional methods for drying wet solids can be used to dry the support, such as for example air drying, inert gas drying, vacuum drying, etc.

In an embodiment, the support can be dried, vacuum dried, or combinations thereof. In an embodiment, the support can be dried in air or a gas, such as for example nitrogen, hydrogen, oxygen, or any inert gas (e.g., argon), or any compatible combinations thereof. As an example, it can be desirable to dry the support in the presence of a gas comprising nitrogen, oxygen or both, for example enriched air or diluted air, such that it contains from about 0.1 vol. % to about 100 vol. % nitrogen, alternatively from about 0.1 vol. % to about 60 vol. % nitrogen, alternatively from about 0.1 vol. % to about 30 vol. % nitrogen. In an embodiment, the gas is a mixture of air and nitrogen. The air or gas can be circulating, moving, or static. In an embodiment, during drying the support particles can be stationary, or moving, such as for example in a rotary dryer. In an embodiment, the support can be dried (e.g., in air, an inert gas, or mixtures thereof) at a temperature of from about 0° C. to about 300° C., alternatively from about 15° C. to about 200° C., alternatively from about 20° C. to about 150° C., alternatively from about 25° C. to about 100° C., or alternatively at ambient temperature; at a pressure of from about 0.01 mmHg to about 500 psig, alternatively from about 0.01 mmHg to about 50 psig, alternatively from about 0.01 mmHg to about 5 psig, or alternatively at sub-ambient pressure, also referred to as vacuum drying; and for a time period of from about 0.1 hours to about 100 hours, alternatively from about 1 hour to about 48 hours, or alternatively from about 4 hours to about 24 hours. In an embodiment, the support can be dried at a temperature of from about 95° C. to about 200° C., alternatively from about 95° C. to about 150° C., or alternatively from about 100° C. to about 135° C. In an embodiment, the support can be vacuum dried at a temperature of from about 15° C. to about 150° C., alternatively from about 30° C. to about 100° C., or alternatively from about 60° C. to about 100° C.; and for a time period of from about 0.1 hours to about 100 hours, alternatively from about 0.5 hours to about 20 hours, or alternatively from about 1 hour to about 10 hours.

During the drying step, the temperature can be optionally increased from ambient temperature to the desired drying temperature in a controlled manner, preferably through a series of temperature increases followed by temperature hold periods (e.g., stepwise).

In an embodiment, the support (e.g., extruded support, extruded zeolitic support, zeolitic support, dried extruded support, dried extruded zeolitic support, dried zeolitic support, etc.) can be thermally treated (e.g., calcined), thereby forming a calcined support (e.g., calcined extruded support, calcined extruded zeolitic support, calcined zeolitic support, etc.).

In an embodiment, the zeolitic support can be subjected to a step of thermally treating (e.g., calcining) the support prior to the step of contacting the zeolitic support with the metal-containing compound and the boron-containing compound.

In an embodiment, the zeolitic support can be calcined (e.g., thermally treated) to form a calcined zeolitic support. Thermal treatment or calcination can be carried out in stationary or flowing gas (e.g., hydrogen, oxygen, air, helium, nitrogen, argon, etc.). For example, the calcination can be carried out in a flowing gas comprising nitrogen and oxygen (for example, air, nitrogen diluted air, or combinations thereof). In an embodiment, during calcining, the support particles can be stationary, or moving, such as for example in a rotary dryer. During the calcination step, the temperature can be optionally increased from ambient temperature or the drying temperature to a desired calcination temperature in a controlled manner, preferably through a series of temperature increases followed by temperature hold periods (e.g., stepwise). Calcination temperatures can range from about 25° C. to about 1000° C., alternatively from about 100° C. to about 900° C., or alternatively from about 250° C. to about 850° C. Calcination pressures can range from about ambient to about 500 psig. Calcination times can range from about 0.5 hours to about 40 hours, alternatively from about 1 hour to about 24 hours, or alternatively from about 4 hour to about 16 hours. In some embodiments, the calcination can be carried out in an oxygen containing atmosphere, wherein the oxygen concentration can be from about 0.01 mol % to about 20 mol % alternatively from about 0.1 mol % to about 15 mol % alternatively from about 0.2 mol % to about 10 mol %, alternatively from about 0.5 mol % to about 5 mol %, or alternatively from about 1 mol % to about 3 mol %. The calcined zeolitic support can be directly used in an aromatization catalyst preparation or can be further processed.

In some embodiments, optional washing steps can follow the thermal treatment, e.g., calcining. For example, the calcined support can be washed with water at temperatures of from about 20° C. to about 100° C. for a time period of from about 1 minute to about 2 hours to produce a washed calcined support (e.g., washed calcined zeolitic support, washed calcined extruded zeolitic support). The washing steps can be repeated from about one to about four times. In an embodiment, the washing can utilize hot distilled or deionized water and occurs after drying, calcining, or both. Following the washing step, the support can optionally undergo another exposure to an elevated temperature of from about 50° C. to about 900° C. for a time period of from about 0.5 to about 20 hours to remove any unwanted moisture. In an embodiment, the support can be calcined following the washing step, such as for example at calcination temperatures of from about 25° C. to about 1,000° C., for calcination times of from about 0.5 hours to about 40 hours.

In an embodiment, the method of preparing an aromatization catalyst can comprise the step of contacting a zeolitic support with a metal-containing compound and a boron-containing compound to produce an impregnated support (e.g., a metal-boron containing zeolitic support). In an embodiment, the zeolitic support (e.g., dried zeolitic support, aged zeolitic support, calcined zeolitic support, washed calcined zeolitic support, etc.) can be contacted with a metal-containing compound prior to, concurrent with, or subsequent to contacting the zeolitic support with the boron-containing compound.

In an embodiment, the zeolitic support can be contacted with a metal-containing compound concurrent with contacting the zeolitic support with the boron-containing compound. In such embodiment, the zeolitic support can be contacted with (e.g., impregnated with) an impregnating composition (e.g., zeolitic support impregnating solution) comprising both the metal-containing compound and the boron-containing compound.

In an embodiment, contacting the zeolitic support with the metal-containing compound and the boron-containing compound can comprise impregnating the zeolitic support with an impregnating composition comprising the metal-containing compound and the boron-containing compound. In an embodiment, the zeolitic support can be contacted with the impregnating composition (e.g., zeolitic support impregnating solution) by soaking the zeolitic support in the impregnating composition. In an embodiment, the zeolitic support can be contacted with the impregnating composition by incipient wetness impregnation of the zeolitic support with the impregnating composition. As will be appreciated by one of skill in the art, and with the help of this disclosure, during incipient wetness impregnation of a support (e.g., zeolitic support), pores of the support become substantially filled with a liquid solution (e.g., impregnating composition, zeolitic support impregnating solution, etc.).

In an embodiment, the boron-containing compound can be present in the impregnating composition at a boron:metal atomic ratio of from about 0.5:1 to about 20:1, alternatively from about 0.5:1 to about 10:1, alternatively from about 0.5:1 to about 5:1, alternatively from about 0.5:1 to about 3:1, alternatively from about 0.5:1 to about 2:1, or alternatively from about 0.5:1 to about 1:1.

In an embodiment, the zeolitic support can be contacted with a metal-containing compound to produce a metal-containing zeolitic support (e.g., Pt-containing zeolitic support). In an embodiment, the metal-containing compound can be any suitable compound comprising a catalytically active metal of the type described previously herein as part of the aromatization catalyst (e.g., a Group 8, Group 9, or Group 10 transition metal). In an embodiment, the metal-containing compound can be any suitable compound comprising iron, cobalt, nickel, ruthenium, rhodium, palladium, osmium, iridium, platinum, or combinations thereof. In an embodiment, the metal-containing compound can comprise a Group 8 transition metal.

In an embodiment, the metal-containing compound can comprise platinum (Pt). Hereafter, for simplicity the disclosure will refer to the metal (e.g., catalytically active metal) as platinum, although it should be understood that any other suitable catalytically active metals (e.g., a Group 8, Group 9, or Group 10 transition metal) could be employed for producing an aromatization catalyst. In an embodiment, the metal-containing compound can comprise a Pt-containing compound. In an embodiment, the Pt-containing compound can be any decomposable Pt-containing compound. Nonlimiting examples of Pt-containing compounds suitable for use with the present disclosure include ammonium tetrachloroplatinate, chloroplatinic acid, diammineplatinum (II) nitrite, bis-(ethylenediamine)platinum (II) chloride, platinum (II) acetylacetonate, dichlorodiammine platinum, platinum (II) chloride, tetraammineplatinum (II) hydroxide, tetraammineplatinum (II) chloride, tetraammineplatinum (II) nitrate, and the like, or combinations thereof.

In an embodiment, the catalytically active metal can be contacted with, that is added to, the zeolitic support by any suitable method, such as incipient wetness impregnation or ion exchange with a solution (e.g., an aqueous solution such as a zeolitic support impregnating solution, an aqueous zeolitic support impregnating solution) of a metal-containing compound. In an embodiment, the metal-containing compound can be a component of an aqueous zeolitic support impregnating solution. A nonlimiting example of a metal-containing solution suitable for use with the present disclosure includes a solution comprising a metal, e.g., a solution comprising platinum.

In an embodiment, a metal (e.g., catalytically active metal) can be present in the impregnating composition in an amount of from about 0.5 wt. % to about 10 wt. %, alternatively from about from about 1.0 wt. % to about 5.0 wt. %, or alternatively from about 2.0 wt. % to about 3.0 wt. %, based on the total weight of the impregnating composition.

In an embodiment, a metal-containing compound can be present in the impregnating composition in an amount of from about 1 wt. % to about 15 wt. %, alternatively from about from about 2.0 wt. % to about 10.0 wt. %, or alternatively from about 3.0 wt. % to about 6.0 wt. %, based on the total weight of the impregnating composition.

In an embodiment, the zeolitic support can be contacted with a boron-containing compound to produce a boron-containing zeolitic support. In an embodiment, the boron-containing compound can be water-soluble. For purposes of the disclosure herein, "water-soluble" refers to equal to or greater than about 0.5 wt. % of a given compound (e.g., boron-containing compound), alternatively equal to or greater than about 1 wt. %, alternatively equal to or greater than about 5 wt. %, alternatively equal to or greater than about 10 wt. %, or alternatively equal to or greater than about 15 wt. % solubility in water at ambient temperature, wherein the wt. % is based on the total weight of the solution obtained by dissolving the given compound in water.

In an embodiment, the boron-containing compound can be contacted with, that is added to, the zeolitic support by any suitable method, such as via impregnation (e.g., soaking, incipient wetness impregnation) with a solution of a boron-containing compound. In an embodiment, the boron-containing compound can be a component of an aqueous zeolitic support impregnating solution.

In an embodiment, the boron-containing compound should not be a Brønsted acid. A Brønsted acid is a substance capable of donating protons, e.g., generate free H. Without wishing to be limited by theory, free $H^+$ could ion exchange with alkali metal cations and alkaline earth cations (e.g., potassium) in the zeolitic support or zeolite (e.g., L-zeolite) and generate acidic sites on the zeolite; and such acidic sites on the zeolite could affect aromatization catalyst performance by lowering platinum dispersion. Further, without wishing to be limited by theory, the presence of free H+ during aromatization catalyst preparation could affect catalyst performance by decreasing selectivity to liquid products due to increasing cracking to light gasses, wherein such cracking can also lead to higher catalyst temperatures, owing to predominant exothermic cracking reactions versus endothermic aromatization reactions. As will be appreciated by one of skill in the art, and with the help of this disclosure, higher aromatization catalyst temperatures and increased cracking can lead to increased coking and faster loss of catalyst activity.

In an embodiment, the boron-containing compound can be a compound characterized by at least one of formulas: $B(OR)_3$, wherein R can comprise an alkyl group, a cycloalkyl, or an aryl group; $H_mB(OR)_n$, wherein R can comprise an alkyl group, a cycloalkyl, or an aryl group, wherein m and n are integers from 0 to 3, and wherein the sum of m and n is 3; $B(OR')_3N$, wherein R' is a $C_1$ to $C_4$ alkyl group; or combinations thereof.

Nonlimiting examples of boron-containing compounds suitable for use with the present disclosure include triethanolamine borate, elemental boron, boric acid, boron bromide, boron carbide, boron fluoride, boron nitride, boron oxide, carborane, N,N-dimethylanilinium tetra(pentafluorophenyl)borate, methyl oxazaborolidine, nitronium tetrafluoroborate, phenylboron dichloride, phenylboron dihydroxide, potassium dodecahydrododecaborate hydrate, potassium tri-sec-butylborohydride, sodium cyanoborohydride, tetrafluoroboric acid, tri-n-amylborate, B-triboromoborazine, tri-n-butylborate, B-trichloroborazine, triethanolamineborate, triethylborate, triethylboron, trimethyoxyboroxine, trimethylborate, trimethylboron, triphenylboron, triphenylboron sodium hydroxide, tris(pentafluorophenyl)boron, tris(trimethylsiloxy)boron, triethylammonium dodecahydrododecaborate, bis(pinacolata)diboron, borane complexes, or combinations thereof.

In an embodiment, boron can be present in the impregnating composition (e.g., zeolitic support impregnating solution) in an amount of from about 0.1 wt. % to about 5 wt. %, alternatively from about from about 0.5 wt. % to about 3 wt. %, or alternatively from about 1 wt. % to about 2 wt. %, based on the total weight of the impregnating composition.

In an embodiment, the boron-containing compound can be present in the impregnating composition (e.g., zeolitic support impregnating solution) in an amount of from about 5 wt. % to about 25 wt. %, alternatively from about from about 10 wt. % to about 20 wt. %, or alternatively from about 15 wt. % to about 18 wt. %, based on the total weight of the impregnating composition.

In an embodiment, the zeolitic support can be contacted with a thulium-containing compound to produce a thulium-containing zeolitic support. In an embodiment, the thulium-containing compound can be water-soluble.

In an embodiment, the thulium-containing compound can be contacted with, that is added to, the zeolitic support by any suitable method, such as via impregnation (e.g., soaking, incipient wetness impregnation) with a solution of a thulium-containing compound. In an embodiment, the thulium-containing compound can be a component of an aqueous solution (e.g., zeolitic support impregnating solution).

Nonlimiting examples of thulium-containing compounds suitable for use with the present disclosure include thulium (III) chloride, thulium (III) bromide, thulium (III) acetate, thulium (III) nitrate, and the like, or combinations thereof.

In an embodiment, thulium can be present in the impregnating composition (e.g., zeolitic support impregnating solution) in an amount of from about 0.5 wt. % to about 10 wt. %, alternatively from about from about 1.0 wt. % to about 5.0 wt. %, or alternatively from about 2.0 wt. % to about 3.0 wt. %, based on the total weight of the impregnating composition.

In some embodiments, the impregnated support can be aged to form an aged impregnated support (e.g., an aged impregnated zeolitic support). In such embodiments, aging of the impregnated support can be performed at temperatures of from about sub-ambient temperatures (e.g., below room temperature) to about 200° C.; at pressures of from about ambient pressure (e.g., atmospheric pressure) to about 500 psig; for time periods of from about 1 minute to about 10 days; and under conditions where the impregnated support can be either stationary or moving.

In an embodiment, the impregnated support (e.g., metal-containing zeolitic support, boron-containing zeolitic support, metal-boron containing zeolitic support, platinum-boron containing zeolitic support, etc.) contains non-framework boron, that is the boron does not participate in the crystal structure of the zeolitic support that is part of the impregnated support.

In an embodiment, the impregnated support can be aged, dried, calcined, or combinations thereof (e.g., thermally treated) prior to further processing. In such embodiment, aging, drying, calcining, or combinations thereof can be performed by using the methods and conditions (e.g., temperatures, time ranges, oxygen concentration, etc.) described previously herein for aging, drying, calcining, or combinations thereof the zeolitic support.

In an embodiment, the impregnated support can be thermally treated to produce a thermally treated impregnated support prior to further processing. In an embodiment, the impregnated support can be dried to produce a dried impregnated support prior to further processing. While the present disclosure is discussed in detail in the context of drying or otherwise thermally treating the impregnated support prior to further processing, it should be understood that in some instances the impregnated support could be subjected to further processing without drying or otherwise thermally treating the impregnated support.

In an embodiment, the impregnated support can be subjected to a step of aging and drying the support to produce a dried aged impregnated support prior to the step of contacting an impregnated support with an activating composition. In an embodiment, the impregnated support can be subjected to a step of thermally treating (e.g., calcining) the support to produce a calcined impregnated support prior to the step of contacting an impregnated support with an activating composition.

In an embodiment, the method of preparing an aromatization catalyst can comprise the step of contacting the impregnated support (e.g., dried or thermally treated impregnated support, dried impregnated support, dried aged impregnated support, calcined dried aged impregnated support) with an activating composition to produce an impregnated activated support. In an embodiment, the dried or thermally treated impregnated support (e.g., dried impregnated zeolitic support, dried aged impregnated zeolitic support, calcined impregnated zeolitic support) can be activated by contacting the dried or thermally treated impregnated support with an activating composition.

In an embodiment, the dried or thermally treated impregnated support (e.g., dried impregnated zeolitic support, dried aged impregnated zeolitic support, calcined impregnated zeolitic support) can be activated by a number of processes generally referred to as halogenation. Halogenation of dried or thermally treated impregnated support can be carried out by contacting the impregnated support with an activating composition of the type and under the conditions described herein, to produce an impregnated activated support, wherein the activating composition can comprise one or more halide-containing compounds, such as for example a chlorine-containing compound or a fluorine-containing compound.

In an embodiment, the dried or thermally treated impregnated support (e.g., dried impregnated zeolitic support, dried aged impregnated zeolitic support, calcined impregnated zeolitic support) can be contacted with an activating composition over a time period of from about 0.1 hours to about 50 hours, alternatively from about 1 hour to about 20 hours, or alternatively from about 2 hours to about 10 hours, at a temperature in the range of from about 15° C. to about 1000° C., alternatively from about 100° C. to about 500° C., alternatively from about 200° C. to about 900° C., alternatively from about 100° C. to about 800° C., alternatively from about 200° C. to about 450° C., or alternatively from about 300° C. to about 400° C.

In some embodiments, the dried or thermally treated impregnated support (e.g., dried impregnated zeolitic support, dried aged impregnated zeolitic support, calcined impregnated zeolitic support) can be contacted with an activating composition by a number of processes generally referred to as chlorination, wherein the activation composition can comprise a chlorine-containing compound. Chlorination of impregnated support can be carried out by contacting the impregnated support with an activating composition of the type and under the conditions described herein, to produce an impregnated activated support (e.g., chlorinated metal-boron containing zeolitic support, chlorinated platinum-boron containing zeolitic support, etc.).

In other embodiments, the dried or thermally treated impregnated support (e.g., dried impregnated zeolitic support, dried aged impregnated zeolitic support, calcined impregnated zeolitic support) can be activated by a number of processes generally referred to as fluorination, wherein the activation composition can comprise a fluorine-containing compound. Fluorination of the impregnated support can be carried out by contacting the impregnated support with an activating composition of the type and under the conditions described herein, to produce an impregnated activated support (e.g., fluorinated metal-boron containing zeolitic support, fluorinated platinum-boron containing zeolitic support, etc.).

In yet other embodiments, the dried or thermally treated impregnated support (e.g., dried impregnated zeolitic support, dried aged impregnated zeolitic support, calcined impregnated zeolitic support) can be activated by a number of processes generally referred to as chlorofluorination, wherein the activation composition can comprise both a chlorine-containing compound and a fluorine-containing compound. Chlorofluorination of the dried or thermally treated impregnated support (e.g., dried impregnated zeolitic support, dried aged impregnated zeolitic support, calcined impregnated zeolitic support) can be carried out by contacting the dried or thermally treated impregnated support with an activating composition of the type and under the conditions described herein, to produce an impregnated activated support (e.g., fluorinated chlorinated metal-boron containing zeolitic support, fluorinated chlorinated platinum-boron containing zeolitic support, etc.).

In an embodiment, the chlorofluorination can occur in gas phase (e.g., gaseous activation, gaseous chlorofluorination). In such embodiments, the support (e.g., impregnated support) can be dried under ambient pressure (as opposed to vacuum drying) prior to the gaseous halogenation (e.g., chlorofluorination). As will be appreciated by one of skill in the art, and with the help of this disclosure, it is preferable to dry the support. Without wishing to be limited by theory, drying the support avoids formation of by-products from the chlorine-containing compound or fluorine-containing compound, such as for example formation of ammonium hydroxide, ammonium bifluoride, or both from aqueous ammonium fluoride.

In some embodiments, the activation can comprise a sequential halogenation. For example, the support can be chlorinated, followed by fluorination. Alternatively, for example, the support can be fluorinated, followed by chlorination.

In other embodiments, the activation can comprise a simultaneous halogenation, wherein the chlorination and the fluorination occur at the same time.

In an embodiment, the halide-containing compound can comprise an organic ammonium halide, an ammonium halide, and the like, or combinations thereof.

In an embodiment, the organic ammonium halide can comprise one or more compounds represented by formula $N(R^1_wR^2_xR^3_yR^4_z)X$; wherein $R^1$, $R^2$, $R^3$, and $R^4$ can be methyl, ethyl, propyl, butyl, or combinations thereof; wherein w, x, y, z can be any integer from 0 to 4 provided that $w+x+y+z=4$; and wherein X is a halide.

Nonlimiting examples of organic ammonium halides suitable for use in the present disclosure include tetraalkylammonium halides, tetraalkylammonium chlorides, tetraalkylammonium fluorides, tetramethylammonium chloride, tetramethylammonium fluoride, tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, and the like, or combinations thereof.

In an embodiment, the halide-containing compound can comprise an ammonium halide, such as for example ammonium chloride ($NH_4Cl$ or AC), ammonium fluoride ($NH_4F$ or AF), or combinations thereof.

In an embodiment, a first halide-containing compound can comprise a tetraalkylammonium halide and a second halide-containing compound can comprise an ammonium halide. In some embodiments, a first halide-containing compound can comprise a tetraalkylammonium chloride and a second halide-containing compound can comprise ammonium fluoride. In other embodiments, a first halide-containing compound can comprise ammonium chloride and a second halide-containing compound can comprise ammonium fluoride.

In an embodiment, the activating composition can comprise one or more halide-containing compounds, such as for example a chlorine-containing compound. In an embodiment, the chlorine-containing compound can be a gas (e.g., gas-phase halogenation or chlorination), a liquid (e.g., liquid-phase halogenation or chlorination), or combinations thereof.

In an embodiment, the impregnated support can be contacted with a liquid chlorine-containing compound to produce an impregnated activated support. Such a liquid chlorine-containing compound can comprise at least one chlorine-containing compound.

Nonlimiting examples of liquid chlorine-containing compounds suitable for use in the present disclosure include ammonium chloride; one or more compounds represented by formula $N(R^1_wR^2_xR^3_yR^4_z)Cl$, wherein $R^1$, $R^2$, $R^3$, and $R^4$ can be methyl, ethyl, propyl, butyl, or combinations thereof, and wherein w, x, y, z can be any integer from 0 to 4 provided that w+x+y+z=4; or combinations thereof.

In some embodiments, the compounds represented by the formula $N(R^1_wR^2_xR^3_yR^4_z)Cl$ can comprise ammonium chloride, methyl ammonium chloride, tetramethylammonium chloride, tetraethylammonium chloride, tetrapropylammonium chloride, tetrabutylammonium chloride, methyltriethylammonium chloride, and the like, or combinations thereof.

In an embodiment, the activating composition can comprise a solution of a chlorine-containing compound. The solution of the chlorine-containing compound can comprise any suitable solvent. In an embodiment, the liquid chlorine-containing compound can comprise an ammonium chloride solution (e.g., an aqueous ammonium chloride solution).

In an embodiment, the impregnated support can be contacted with a liquid chlorine-containing compound in any suitable manner, such as for example by incipient wetness impregnation. During incipient wetness impregnation, the pores of the impregnated support become substantially filled with the liquid chlorine-containing compound. Other contacting methods such as soaking can also be employed to contact the impregnated support with the liquid chlorine-containing compound to produce an impregnated activated support.

In an embodiment the impregnated support can be contacted with a liquid chlorine-containing compound (e.g., an ammonium chloride solution) at temperatures ranging from about 0° C. to about 200° C., alternatively from about 20° C. to about 100° C., or alternatively from about 40° C. to about 60° C. for a time period of from about 1 minute to about 100 hours, alternatively from about 0.1 hours to about 50 hours, or alternatively from about 1 hour to about 24 hours.

In an alternative embodiment, the impregnated support can be contacted with a gaseous chlorine-containing compound or gas-phase chlorine-containing compound (e.g., gaseous chlorination, gaseous chlorofluorination) to produce an impregnated activated support. Such a gaseous chlorine-containing compound can comprise at least one chlorine-containing compound.

In an embodiment, the liquid or solid chlorine-containing compounds (e.g., ammonium chloride, compounds represented by the formula $N(R^1_wR^2_xR^3_yR^4_z)Cl$, or combinations thereof) could be heated and transferred into a gas-phase, and used as gaseous chlorine-containing compounds. Without wishing to be limited by theory, it is possible that the solid-phase chlorine-containing compounds sublime and migrate into the impregnated support to produce an impregnated activated support.

Nonlimiting examples of gaseous chlorine-containing compounds suitable for use in the present disclosure include ammonium chloride, methyl ammonium chloride, tetramethylammonium chloride, tetraethylammonium chloride, tetrapropylammonium chloride, tetrabutylammonium chloride, methyltriethylammonium chloride, and the like, or combinations thereof. In an embodiment, the gaseous chlorine-containing compound can comprise ammonium chloride.

In an embodiment, the impregnated support can be contacted with a gaseous chlorine-containing compound in any suitable manner, such as for example by heating the impregnated support in the presence of a gaseous chlorine-containing compound (e.g., ammonium chloride) and optionally in the presence of a carrier gas (e.g., nitrogen) to produce an impregnated activated support. In an embodiment, the impregnated support can be contacted with a gaseous chlorine-containing compound at temperatures of from about 100° C. to about 500° C. for a time period of from about 0.2 hours to about 20 hours.

In an embodiment, the activating composition can further comprise a carrier gas. In such embodiment, the carrier gas can be used for diluting the gaseous chlorine-containing compound (e.g., ammonium chloride) during the gaseous chlorination (e.g., gaseous chlorofluorination). In some embodiments, the carrier gas can comprise an inert gas, argon, helium, nitrogen, and the like, or combinations thereof. In other embodiments, the carrier gas can comprise air. In yet other embodiments, the carrier gas can comprise nitrogen and oxygen. In still yet other embodiments, the carrier gas can comprise hydrogen.

In an embodiment, the carrier gas can comprise nitrogen.

In an embodiment, the activating composition can comprise one or more halide-containing compounds, such as for example a fluorine-containing compound. In an embodiment, the fluorine-containing compound can be a gas (e.g., gas-phase halogenation or fluorination), a liquid (e.g., liquid-phase halogenation or fluorination), or combinations thereof.

In an embodiment, the impregnated support can be contacted with a liquid fluorine-containing compound to produce an impregnated activated support. Such a liquid fluorine-containing compound can comprise at least one fluorine-containing compound.

Nonlimiting examples of liquid fluorine-containing compounds suitable for use in the present disclosure include ammonium fluoride; one or more compounds represented by formula $N(R^1_wR^2_xR^3_yR^4_z)F$, wherein $R^1$, $R^2$, $R^3$, and $R^4$ can be methyl, ethyl, propyl, butyl, or combinations thereof, and wherein w, x, y, z can be any integer from 0 to 4 provided that w+x+y+z=4; or combinations thereof.

In some embodiments, the compounds represented by the formula $N(R^1_wR^2_xR^3_yR^4_z)F$ can comprise ammonium fluoride, methyl ammonium fluoride, tetramethylammonium fluoride (TMAF), tetraethylammonium fluoride (TEAF), tetrapropylammonium fluoride, tetrabutylammonium fluoride, methyltriethylammonium fluoride, and the like, or combinations thereof.

In an embodiment, the activating composition can comprise a solution of a fluorine-containing compound. The solution of the fluorine-containing compound can comprise any suitable solvent. In an embodiment, the liquid fluorine-containing compound can comprise an ammonium fluoride solution (e.g., an aqueous ammonium fluoride solution).

In an embodiment, the impregnated support can be contacted with a liquid fluorine-containing compound in any suitable manner, such as for example by incipient wetness impregnation. During incipient wetness impregnation, the pores of the impregnated support become substantially filled with the liquid fluorine-containing compound. Other contacting methods such as soaking can also be employed to contact the impregnated support with the liquid fluorine-containing compound to produce an impregnated activated support.

In an embodiment, the impregnated support can be contacted with a liquid fluorine-containing compound (e.g., an ammonium fluoride solution) at temperatures ranging from about 0° C. to about 200° C., alternatively from about 20° C. to about 100° C., or alternatively from about 40° C. to about 60° C. for a time period of from about 1 minute to about 100 hours, alternatively from about 0.1 hours to about 50 hours, or alternatively from about 1 hour to about 24 hours.

In an alternative embodiment, the impregnated support can be contacted with a gaseous fluorine-containing compound or gas-phase fluorine-containing compound (e.g., gaseous fluorination, gaseous chlorofluorination) to produce an impregnated activated support. Such a gaseous fluorine-containing compound can comprise at least one fluorine-containing compound.

In an embodiment, the liquid or solid fluorine-containing compounds (e.g., ammonium fluoride, compounds represented by the formula $N(R^1_wR^2_xR^3_yR^4_z)F$, or combinations thereof) could be heated and transferred into a gas-phase, and used as gaseous fluorine-containing compounds. Without wishing to be limited by theory, it is possible that the solid-phase fluorine-containing compounds sublime and migrate into the impregnated support to produce an impregnated activated support.

Nonlimiting examples of gaseous fluorine-containing compounds suitable for use in the present disclosure include ammonium fluoride, methyl ammonium fluoride, tetramethylammonium fluoride, tetraethylammonium fluoride, tetrapropylammonium fluoride, tetrabutylammonium fluoride, methyltriethylammonium fluoride, and the like, or combinations thereof. In an embodiment, the gaseous fluorine-containing compound can comprise ammonium fluoride.

In an embodiment, the impregnated support can be contacted with a gaseous fluorine-containing compound in any suitable manner, such as for example by heating the impregnated support in the presence of a gaseous fluorine-containing compound (e.g., ammonium fluoride) and optionally in the presence of a carrier gas (e.g., nitrogen) to produce an impregnated activated support. In an embodiment, the impregnated support can be contacted with a gaseous fluorine-containing compound at temperatures of from about 100° C. to about 500° C. for a time period of from about 1 minute to about 1000 hours, alternatively from about 0.1 hours to about 50 hours, or alternatively from about 1 hour to about 24 hours.

In an embodiment, the activating composition can further comprise a carrier gas. In such embodiment, the carrier gas can be used for diluting the gaseous fluorine-containing compound (e.g., ammonium fluoride) during the gaseous fluorination (e.g., gaseous chlorofluorination). In some embodiments, the carrier gas can comprise an inert gas, argon, helium, nitrogen, and the like, or combinations thereof. In other embodiments, the carrier gas can comprise air. In yet other embodiments, the carrier gas can comprise nitrogen and oxygen. In still yet other embodiments, the carrier gas can comprise hydrogen.

In an embodiment, the carrier gas can comprise nitrogen.

In an embodiment, the impregnated activated support contains non-framework boron; that is boron does not participate in the crystal structure of the aluminosilicate that is part of the zeolitic support.

In an embodiment, the impregnated activated support can be aged, dried, calcined, or combinations thereof (e.g., thermally treated) prior to further processing to produce a calcined impregnated activated support. In such embodiment, aging, drying, calcining, or combinations thereof can be performed by using the methods or conditions (e.g., temperatures, time ranges, oxygen concentration, etc.) described previously herein for aging, drying, calcining, or combinations thereof the zeolitic support.

In an embodiment, the impregnated activated support can be subjected to a step of thermally treating (e.g., calcining) the support prior to any other further processing of the impregnated activated support. For purposes of the disclosure herein, the impregnated activated support that has been subjected to aging, drying, calcining, or combinations thereof will be referred to as an "aromatization catalyst."

In an embodiment, the impregnated support can be contacted with the activating composition prior to, concurrent with, or subsequent to the step of thermally treating the support. In an embodiment, the impregnated support can be contacted with the activating composition concurrent with thermally treating the support.

In some embodiments, the impregnated support can be contacted simultaneously with a chlorine-containing compound, a fluorine-containing compound, or both to produce an impregnated activated support. In such embodiments, the activating composition can comprise a gaseous chlorine-containing compound, a gaseous fluorine-containing compound, or both, such as for example ammonium chloride and ammonium fluoride. Alternatively, the activating composition can comprise a liquid chlorine-containing compound, a liquid fluorine-containing compound, or both such as for example a solution of ammonium chloride and ammonium fluoride.

In other embodiments, the impregnated support can be contacted with the chlorine-containing compound (e.g., chlorination) prior to contacting the support with the fluorine-containing compound (e.g., fluorination).

In yet other embodiments, the impregnated support can be contacted with the fluorine-containing compound (e.g., fluorination) prior to contacting the support with the chlorine-containing compound (e.g., chlorination).

In still yet other embodiments, the zeolitic support can be simultaneously contacted with the metal-containing compound, the boron-containing compound, and the activating composition to produce an impregnated activated support, wherein the activation composition can comprise a chlorine-containing compound, a fluorine-containing compound, or both. In such embodiments, the impregnated activated support can be further aged, dried, calcined, or combinations thereof to produce the aromatization catalyst.

In some embodiments, the zeolitic support can be simultaneously contacted with the metal-containing compound, the thulium-containing compound, and the activating composition to produce an impregnated activated support, wherein the activation composition can comprise a chlorine-containing compound, a fluorine-containing compound, or both. In such embodiments, the impregnated activated support can be further aged, dried, calcined, or combinations thereof to produce the aromatization catalyst.

In an embodiment, the zeolitic support can be simultaneously contacted with the metal-containing compound and the thulium-containing compound to form the thermally treated impregnated support (e.g., Pt/Tm-impregnated support). In such embodiment, the Pt/Tm-impregnated support can be further contacted with an activating composition to produce an impregnated activated support.

In another embodiment, the zeolitic support can be contacted with the metal-containing compound prior to contacting the support with the thulium-containing compound, to form the impregnated support (e.g., Pt/Tm-impregnated support). In such embodiment, the Pt/Tm-impregnated support can be further contacted with an activating composition to produce an impregnated activated support.

In still another embodiment, the zeolitic support can be contacted with the thulium-containing compound prior to contacting the support with the metal-containing compound, to form the impregnated support (e.g., Pt/Tm-impregnated support). In such embodiment, the Pt/Tm-impregnated support can be further contacted with an activating composition to produce an impregnated activated support.

As will be appreciated by one of skill in the art, and with the help of this disclosure, the steps of the method of preparing an aromatization catalyst can be used in any suitable order to produce the aromatization catalyst.

In an embodiment, the aromatization catalyst can be contacted with a hydrocarbon feed in an aromatization process to produce aromatic compounds (e.g., benzene, toluene, xylenes, and mixtures thereof). In an embodiment, the aromatization catalyst and the hydrocarbon feed can be contacted under conditions suitable for conversion of at least a portion of the hydrocarbons to aromatic compounds.

In an embodiment, the aromatization catalyst prepared as disclosed herein can be used as a catalyst in an aromatization reactor system comprising at least one aromatization reactor and its corresponding processing equipment. As used herein, the terms "aromatization," "aromatizing" and "reforming" refer to the treatment of a hydrocarbon feed to provide aromatic compounds. In an embodiment, the aromatic compounds can be an aromatics enriched product, wherein the aromatics content of the aromatic product is greater than the aromatics content of the hydrocarbon feed. Typically, one or more hydrocarbons of the feed undergo one or more reforming reactions to produce aromatic compounds. Some of the aromatization reactions that occur during the aromatization operation include the dehydrogenation of cyclohexanes to aromatics, dehydroisomerization of alkylcyclopentanes to aromatics, dehydrocyclization of acyclic hydrocarbons to aromatics, or combinations thereof. A number of other reactions also occur, including the dealkylation of alkylbenzenes, isomerization of paraffins, cracking reactions, hydrocracking reactions that produce light gaseous hydrocarbons (e.g., methane, ethane, propane and butane, or combinations thereof).

In an embodiment, the aromatization reaction occurs under process conditions that favor the dehydrocyclization reaction and limit undesirable cracking reactions (e.g., hydrocracking reactions, hydrodealkylation). The pressures can be from about 0 pound per square inch gauge (psig) to about 500 psig, or alternatively from about 25 psig to about 300 psig. The molar ratio of hydrogen to hydrocarbons can be from about 0.1:1 to about 20:1, or alternatively from about 1:1 to about 6:1. The operating temperatures include reactor inlet temperatures from about 700° F. (371.1° C.) to about 1050° F. (565.5° C.), or alternatively from about 900° F. (482.2° C.) to about 1000° F. (537.7° C.). The liquid hourly space velocity for the hydrocarbon feed over the aromatization catalyst can be from about 0.1 to about 10, or alternatively from about 0.5 to about 2.5.

The composition of the hydrocarbon feed could be considered when designing catalytic aromatization systems. In an embodiment, the hydrocarbon feed can comprise non-aromatic hydrocarbons including linear or branched alkanes, cycloalkanes, or alkenes containing at least six carbon atoms. In another embodiment, the hydrocarbon feed can comprise a naphtha feed. The naphtha feed can be a hydrocarbon feed with a boiling range of from about 70° F. (21.1° C.) to about 450° F. (232.2° C.). The naphtha feed could contain aliphatic, naphthenic, or paraffinic hydrocarbons. These aliphatic and naphthenic hydrocarbons can be converted, at least in part, to aromatics in the aromatization reactor system. While catalytic aromatization typically refers to the conversion of naphtha, other hydrocarbon feeds can be treated as well to provide an aromatics enriched product. Therefore, while the conversion of naphtha is one embodiment, the present disclosure can be useful for activating catalysts for the conversion or aromatization of a variety of hydrocarbon feeds such as paraffinic hydrocarbons, olefinic hydrocarbons, acetylenic hydrocarbons, cyclic paraffin hydrocarbons, cyclic olefin hydrocarbons, and mixtures thereof, and particularly saturated hydrocarbons.

In an embodiment, the hydrocarbon feed can be substantially free of sulfur, nitrogen, metals, and other known poisons for aromatization catalysts. In an embodiment, the hydrocarbon feed contains less than about 100 ppb of sulfur. If present, such poisons can be removed using any suitable methods. For example, the feed can be purified by using conventional hydrofining techniques, using sorbents to remove the remaining poisons, or both.

In an embodiment, the aromatization catalyst as disclosed herein can be characterized by reduced cracking tendency when compared to the cracking tendency of a similar aromatization catalyst lacking the non-framework boron, wherein the reduced cracking tendency can be represented by an increased wt. % of C5+ products, based on the total weight of the products, and wherein the wt. % of C5+ products for the aromatization catalyst is increased by at least about 2 wt. %, alternatively by at least about 3 wt. %, alternatively by at least about 4 wt. %, or alternatively by at least about 5 wt. %, when compared to a similar aromatization catalyst lacking the non-framework boron.

In an embodiment, the aromatization catalyst as disclosed herein can be characterized by a higher yield of aromatic compounds that is increased by at least about 2 wt. %, alternatively by at least about 3 wt. %, or alternatively by at least about 5 wt. %, based on the total weight of the products, when compared to the yield of aromatic compounds of a similar aromatization catalyst lacking the non-framework boron.

In an embodiment, the aromatization catalyst as disclosed herein can be characterized by a selectivity that is increased when compared to the selectivity of a similar aromatization catalyst lacking the non-framework boron. The selectivity of an aromatization catalyst can be defined as the molar ratio of the feed that undergoes an aromatization reaction to the feed that undergoes a cracking reaction in the presence of said aromatization catalyst.

In an embodiment, a method of preparing an aromatization catalyst can comprise (a) contacting a zeolitic support with a metal-containing compound and a boron-containing compound to produce an impregnated support; and (b) contacting the impregnated support with an activating composition comprising a gaseous chlorine-containing compound and a gaseous fluorine-containing compound to produce an aromatization catalyst, wherein the impregnated support is heated in the presence of the activating composition to a temperature in the range of from about 100° C. to about 500° C., and wherein the impregnated support, the aromatization catalyst, or both contain non-framework boron.

In an embodiment, a method of preparing an aromatization catalyst can comprise (a) contacting a zeolitic support with a platinum-containing compound and a boron-containing compound to produce a platinum-boron containing zeolitic support; and (b) contacting the platinum-boron containing zeolitic support with an activating composition comprising a gaseous chlorine-containing compound and a gaseous fluorine-containing compound to produce an aromatization catalyst, wherein the platinum-boron containing zeolitic support is heated in the presence of the activating composition to a temperature in the range of from about 100° C. to about 500° C., and wherein the platinum-boron containing zeolitic support, the aromatization catalyst, or both contain non-framework boron.

In an embodiment, a method of preparing an aromatization catalyst can comprise (a) contacting a zeolitic support with tetraammineplatinum chloride and triethanolamineborate to produce a platinum-boron containing zeolitic support; and (b) contacting the platinum-boron containing zeolitic support with an activating composition comprising gaseous ammonium chloride and gaseous ammonium fluoride to produce an aromatization catalyst, wherein the platinum-boron containing zeolitic support is heated in the presence of the activating composition to a temperature in the range of from about 100° C. to about 500° C., and wherein the platinum-boron containing zeolitic support, the aromatization catalyst, or both contain non-framework boron.

In an embodiment, a method of preparing an aromatization catalyst can comprise (a) extruding a support mixture comprising a zeolite and a binder to form an extruded zeolitic support; (b) drying the zeolitic support to form a dried extruded zeolitic support; (c) calcining the zeolitic support to form a calcined dried zeolitic support (i.e., a zeolitic support); (d) washing the calcined dried zeolitic support from one to three times with water at a temperature of from about 120° F. to about 140° F. to form a washed calcined dried zeolitic support (i.e., a zeolitic support); (e) contacting the zeolitic support with tetraammineplatinum chloride and triethanolamineborate to produce a platinum-boron containing zeolitic support; (f) contacting the platinum-boron containing zeolitic support with an activating composition comprising ammonium chloride and ammonium fluoride to produce an aromatization catalyst, wherein the activating composition is in a solid state, and wherein the activating composition is heated to sublimate the solid activation composition into the zeolitic support; and (g) calcining the aromatization catalyst.

In an embodiment, a method of preparing an aromatization catalyst can comprise (a) contacting a zeolitic support with a platinum-containing compound and a thulium-containing compound to produce a platinum-thulium containing zeolitic support; and (b) contacting the platinum-thulium containing zeolitic support with an activating composition comprising a gaseous chlorine-containing compound and a gaseous fluorine-containing compound to produce an aromatization catalyst, wherein the platinum-thulium containing zeolitic support is heated in the presence of the activating composition to a temperature in the range of from about 100° C. to about 500° C.

In an embodiment, the method of preparing an aromatization catalyst as disclosed herein advantageously displays improvements in one or more process characteristics when compared to an otherwise similar process lacking a step of contacting a zeolitic support with an impregnating composition comprising a boron-containing compound. In an embodiment, the use of a boron-containing compound as disclosed herein can advantageously lead to an aromatization catalyst that can maintain a low cracking profile, which is a catalyst with a low occurrence of cracking reactions, for a longer time period, when compared to a similar aromatization catalyst lacking the boron.

In an embodiment, the use of a boron-containing compound as disclosed herein can advantageously reduce cracking reactions on the aromatization catalyst, when compared to a similar aromatization catalyst lacking the boron.

In an embodiment, the use of a boron-containing compound as disclosed herein can advantageously lead to an aromatization catalyst that can give a higher yield of aromatic compounds, when compared to a similar aromatization catalyst lacking the boron. In an embodiment, the use of a boron-containing compound as disclosed herein can advantageously lead to an aromatization catalyst that can provide a higher selectivity towards aromatic compounds, when compared to a similar aromatization catalyst lacking the boron.

In an embodiment, the use of a boron-containing compound as disclosed herein can advantageously lead to an aromatization catalyst that displays lower fouling, when compared to a similar aromatization catalyst lacking the boron.

In an embodiment, the use of gaseous activation as disclosed herein can advantageously reduce or eliminate the need for silicon (glass)-free equipment. As will be appreciated by one of skill in the art, and with the help of this disclosure, aqueous ammonium fluoride solutions can etch silicon (glass)-containing equipment.

In an embodiment, drying the support (impregnated support) can be advantageously done at ambient pressure (as opposed to vacuum drying). In such embodiment, drying at ambient pressure is more cost effective than vacuum drying, and could lead to an overall lower cost of producing the aromatization catalyst. In an embodiment, an aromatization catalyst wherein the support was dried at ambient pressure prior to the chlorofluorination can advantageously have about the same or better activity as compared to an aromatization catalyst wherein the support was vacuum dried at ambient pressure prior to the chlorofluorination. Additional advantages of the process for the production of an aromatization catalyst as disclosed herein can be apparent to one of skill in the art viewing this disclosure.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

Example 1

The catalytic properties of aromatization catalysts were investigated. More specifically, the catalytic properties (e.g., cracking behavior, C5+ yield, benzene and toluene yield, catalyst fouling, etc.) of aromatization catalysts were investigated in the presence and in the absence of boron within the aromatization catalyst composition.

Aromatization Catalyst Preparation

All aromatization catalysts used in the examples of the present disclosure were prepared by using a washed calcined extruded KL zeolite or zeolitic support as the washed calcined extruded zeolitic support. A washed calcined extruded KL zeolitic support was prepared on a large scale by using a Tosoh zeolite, SI-350 silica sol, and methyl cellulose (METHOCEL™ cellulose ethers) as an extrusion aid. The extrudate (1,800 lbs) was placed in a large tank and covered with wash water (1.5 g/g base), alkaline earths, and sulfur species. The water, which had a pH of 7.3, was added over about 30 min and then drained from the tank over about 30 min. The washed calcined extruded KL zeolitic support was washed twice more in the same way. The resultant material was then dried and calcined at 950° F. in a rotary calciner. The Na content of the final wash water was less than 100 ppm. The washing reduced the Na content of the zeolitic support base from 0.48 wt. % to 0.38 wt. %.

The aromatization catalysts were prepared by two different methods, wherein the washed calcined extruded KL zeolitic support was contacted with the chlorine-containing compound and the fluorine-containing compound either in gas-phase (e.g., gas-phase halogenation) or in liquid-phase (e.g., liquid-phase halogenation).

In an embodiment, the aromatization catalyst was prepared by subjecting a washed calcined extruded KL zeolitic support to incipient wetness impregnation with an aqueous solution containing appropriate amounts of tetraammineplatinum chloride (used as the metal-containing compound) and triethanolamineborate (used as the boron-containing compound) to produce an impregnated support. For example, 20 g of washed calcined extruded KL zeolitic support were impregnated with a solution containing 0.36 g tetraammineplatinum chloride, 7.16 g water, and 2.39 g of an aqueous triethanolamineborate solution with a concentration of 16.8 wt. %. The impregnated support was allowed to stand at ambient temperature in air for 16 hours before it was vacuum dried at 80° C. for 4 hours, followed by static air calcination at 200° C. for 16 hours, to produce a calcined impregnated support. The calcined impregnated support was subjected to chlorofluorination (e.g., gas-phase halogenation) at 350° C. for 1 hour with a gas mixture having the following composition per 10 g of calcined impregnated support: air (100 ml/min); nitrogen ($N_2$) (200 ml/min); 1 mol % $F_2/N_2$ (100 ml/min); $H_2O$ (liquid 3 ml/hour); and tetrachlorethylene (liquid 1.5 ml/hour).

In an embodiment, the aromatization catalyst was prepared by subjecting a washed calcined extruded KL zeolitic support to incipient wetness impregnation (e.g., liquid-phase halogenation) with an aqueous solution containing appropriate amounts of tetraammineplatinum chloride (used as the metal-containing compound); triethanolamineborate (used as the boron-containing compound); ammonium chloride (used as the chlorine-containing compound); and ammonium fluoride (used as the fluorine-containing compound) to produce an impregnated activated support. The impregnated activated support was allowed to stand for 16 hours in air at ambient temperature before it was vacuum dried at 85° C. for 4 hours and then calcined in static air at 350° C. for 2 hours to produce the aromatization catalyst.

Fouling Test Protocol

In an embodiment, the aromatization catalysts were subjected to a fouling test based on the following protocol. The fouling test protocol consisted of operating an isothermal reactor at a reactor pressure of 140 psig. The liquid hourly space velocity (LHSV) of the liquid feed and the hydrogen to hydrocarbon ($H_2$:HC) ratio were set at 3 and 0.5, respectively. LHSV is usually calculated by dividing the flow rate of the liquid reactant by the reactor volume. Before the introduction of liquid feed to the reactor, the aromatization catalyst was first reduced overnight by contacting with $H_2$ at ambient pressures, at a gas hourly space velocity (GHSV) of 9,000, and at a temperature of 950° F. GHSV is usually calculated by dividing the flow rate of the gaseous reactant by the reactor volume. Hydrocarbon feed was then introduced and the aromatization catalyst was then conditioned for about 100 hours under the following conditions: pressure of 140 psig, LHSV of 3, $H_2$:HC ratio of 3. The reactor temperature was then adjusted to maintain a target conversion of 60 wt. % benzene plus toluene in the C5+ fraction of the reactor product.

Cracking Behavior

The characteristics of the aromatization catalysts tested (e.g., catalyst 1 or aromatization catalyst 1; catalyst 2 or aromatization catalyst 2; catalyst 3 or aromatization catalyst 3; catalyst 4 or aromatization catalyst 4; reference catalyst or reference aromatization catalyst) are displayed in Table 1, wherein SOR stands for "start of run;" TOS stands for "time on stream;" EOR stands for "end of run;" FR stands for "fouling rate;" $T_{60}$ is the temperature needed to maintain the wt. % of benzene and toluene in a C5+ liquid product at 60 wt. %; and mF/hr is the measure unit for the fouling rate expressed in mili degrees F. per hour (° F./(hr 1,000)). The reference aromatization catalyst in these examples was an AROMAX® Catalyst, which is available from Chevron Phillips Chemical Company. The reference aromatization catalyst lacked boron.

TABLE 1

| Catalyst | Calculated Catalyst Composition | | | Halogenation | | SOR | | EOR | |
|---|---|---|---|---|---|---|---|---|---|
| | Boron wt. % | Pt wt. % | B:Pt mole ratio | Reagents | Temp. ° C. | $T_{60}$ ° F. | TOS hours | $T_{60}$ ° F. | FR mF/hr |
| Reference | — | — | — | — | — | 921 | 168 | 921 | 15.5 |
| 1 | 0.000 | 1.000 | 0.0 | $NH_4Cl + NH_4F$ | 350 | 917 | 145 | 919 | 23.9 |
| 2 | 0.056 | 1.000 | 1.0 | $NH_4Cl + NH_4F$ | 350 | 901 | 144 | 900 | −6.8 |
| 3 | 0.140 | 1.000 | 2.5 | $NH_4Cl + NH_4F$ | 350 | 907 | 144 | 909 | 12.0 |
| 4 | 0.280 | 1.000 | 5.0 | $NH_4Cl + NH_4F$ | 350 | 923 | 144 | 926 | 21.2 |

Aromatization catalyst 1 was prepared by gas phase halogenation with ammonium halides by sublimation of solid ammonium chloride and ammonium fluoride into the zeolitic support which had previously been impregnated with a solution containing tetraammineplatinum chloride (but lacking the boron-containing compound), then dried and calcined. Aromatization catalysts 2, 3, and 4 were prepared by gas-phase halogenation and contained both platinum and boron. Aromatization catalyst 2, which contained boron, was found superior due to a lower fouling rate to the aromatization catalyst 1, which lacked boron. However, a high content of boron (B:Pt atomic ratio of 5) as the one in aromatization catalyst 4 was found less effective due to a higher fouling rate than aromatization catalyst 2, which had a lower content of boron (B:Pt atomic ratio of 1).

Example 2

The catalytic properties of aromatization catalysts were investigated. More specifically, the catalyst fouling of aromatization catalysts was investigated in the presence and in the absence of boron within the aromatization catalyst composition. Three different types of aromatization catalysts (e.g., catalyst 5 or aromatization catalyst 5; catalyst 6 or aromatization catalyst 6; catalyst 7 or aromatization catalyst 7) were prepared with different amounts of boron using incipient wetness impregnation with tetraammineplatinum chloride and triethanolamineborate followed by gas-phase halogenation, as described in Example 1. Aromatization catalyst 5 had a B:Pt atomic ratio of 1; aromatization catalyst 6 had a B:Pt atomic ratio of 2; and aromatization catalyst 7 had a B:Pt atomic ratio of 5.

Figure 2:
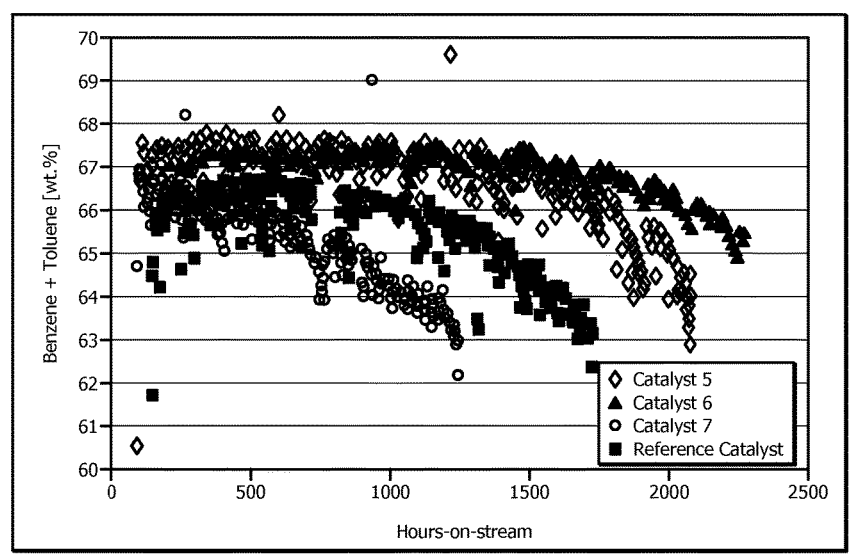
FIG. 2 illustrates a comparison of the amount of benzene and toluene produced over time by aromatization catalysts with different amounts of boron.

The cracking behavior of the aromatization catalysts were analyzed and the data are summarized in FIGS. 1 and 2. The data were collected using the fouling testing protocol as described in Example 1.

C5+ yields displayed in FIG. 1 represent the amount of liquid in the reactor product. Because cracking generates light gases, an increase in the C5+ yield corresponds to a reduction in cracking. When compared to the reference aromatization catalyst, the aromatization catalyst 5 and the aromatization catalyst 6 show a noticeable improvement in the C5+ yield, thus lower cracking. A side benefit of a lower cracking is an increase in the amount of aromatics produced, as shown in FIG. 2.

In contrast, the aromatization catalyst 7 shows the opposite effects of boron. At this high loading of boron (B:Pt atomic ratio of 5), the C5+ yield deteriorates rapidly with time-on-stream and there is a corresponding drop in the aromatics make. The results of the aromatization catalyst 7 suggest that there is a maximum loading for boron beyond which the boron will have a negative impact on the aromatization catalyst.

Example 3

The catalytic properties of aromatization catalysts were investigated. More specifically, the catalyst fouling of aromatization catalysts was investigated in the presence and in the absence of boron within the aromatization catalyst composition. The aromatization catalysts and reference aromatization catalyst were prepared and tested as described in Examples 1 and 2.

FIG. 3 compares the fouling curves of the aromatization catalyst 5, aromatization catalyst 6, and aromatization catalyst 7 with that of the reference aromatization catalyst. A fouling curve represents the temperature, as a function of time-on-stream, required to maintain a target aromatization conversion as the aromatization catalyst deactivates. A fast up-turning curve indicates rapid deactivation and short catalyst life. The aromatization catalyst 5 (B:Pt atomic ratio of 1) had a comparable deactivation rate until late in the run where deactivation was slower than for the reference aromatization catalyst. The aromatization catalyst 5 (B:Pt atomic ratio of 2) exhibited a significantly lower rate of deactivation than the reference aromatization catalyst. Increasing the B:Pt atomic ratio to 5 yielded an aromatization catalyst which deactivated rapidly.

At low loadings of boron (B:Pt atomic ratio of 1 and 2), the shape of the fouling curve had the same curvature as for the reference aromatization catalyst suggesting that boron does not change the deactivation mechanism of the aromatization catalysts, but only slows the rate of coke deposition at the platinum sites. Without wishing to be limited by theory, considering the positive impact boron has on both cracking and fouling rate, it is hypothesized that the boron acts directly on the platinum active sites, which would be consistent with the view that, for a neutral catalyst, hydrocracking occurs mainly on the metal clusters.

Example 4

The catalytic properties of aromatization catalysts were investigated. More specifically, the catalytic behavior of aromatization catalysts (e.g., catalyst 8 or aromatization catalyst 8; catalyst 9 or aromatization catalyst 9) was investigated in the presence and in the absence of boron within the aromatization catalyst composition. The aromatization catalysts were prepared and tested as described in Examples 1 and 2. Aromatization catalyst 8 had a B:Pt atomic ratio of 1 and was prepared by liquid-phase halogenation as described in Example 1. Aromatization catalyst 9 contained no boron and was prepared by gas-phase halogenation as described in Example 1, with 1 wt. % platinum, and without using the boron-containing compound during the incipient wetness impregnation step, prior to the gas-phase chlorofluorination.

Aromatization catalyst 8 was prepared by liquid-phase halogenation using an aqueous solution of ammonium halides, as described in Example 1. The results displayed in FIG. 5 suggest that the type of method of adding the halides (gas-phase halogenation versus liquid-phase halogenation) has a strong influence on the performance of the catalyst. The aromatization catalyst 8 (prepared by liquid-phase halogenation) was inferior to the aromatization catalysts prepared by gas-phase halogenation. The cracking activity of the aromatization catalyst 8 was even slightly higher than that of the reference aromatization catalyst. In spite of this weakness for the aromatization catalyst 8, the effect of the boron can still delay the on-set of the high cracking regime as depicted by the cross-over in the C5+ yields in FIG. 4A, as well as a slightly longer catalyst run-length as seen in FIGS. 4A, 4B and 4C.

Aromatization catalyst 9 (no boron) was tested to see if the gas-phase chlorofluorination procedure itself could reduce cracking regardless of the boron, and the results are displayed in FIG. 5. Surprisingly, the aromatization catalyst 9 had high cracking and deactivated very rapidly. Elemental analysis of the aromatization catalyst 9 revealed the presence of only 0.2% fluoride on the catalyst.

Example 5

The properties of aromatization catalysts were investigated. More specifically, the fouling rate of aromatization catalysts (e.g., catalyst 10 or aromatization catalyst 10; catalyst 11 or aromatization catalyst 11) was investigated for various ways of preparing the catalysts. The aromatization catalysts were prepared and tested as described in Examples 1 and 2. Aromatization catalyst 10 was prepared by liquid-phase halogenation as described in Example 1, by simultaneous incorporation of aqueous solution of tetraammineplatinum chloride, ammonium chloride, and ammonium fluoride. Aromatization catalyst 11 was prepared by gas-phase chlorofluorination as described in Example 1. The wt. % of the catalyst components were measured by X-ray Fluorescence (XRF).

The aromatization catalysts were tested and the data are displayed in Table 2.

TABLE 2

| Catalyst | NH4Cl—NH4F Halogenation Phase | Temperature °C. | Components [wt. %, measured by XRF] | | | SOR T60 °F. | TOS hr | EOR T60 °F. | FR mF/hr |
|---|---|---|---|---|---|---|---|---|---|
| | | | Pt | Cl | F | | | | |
| Reference | — | — | 0.969 | 0.828 | 0.837 | 921 | 168 | 921 | 15.5 |
| 10 | Liquid | 250 | 0.984 | 0.877 | 0.805 | 922 | 144 | 927 | 50.8 |
| 11 | Gas | 250 | 0.985 | 0.912 | 0.896 | 906 | 122 | 908 | 18.6 |

It was surprising to note that halide incorporation through gas-phase ammonium chloride/ammonium fluoride resulted in significant improvement of catalyst activity for aromatization catalyst 11 as compared to aromatization catalyst 10, which was produced by liquid chlorofluorination.

Example 6

The properties of aromatization catalysts were investigated. More specifically, the fouling rate of aromatization catalysts (e.g., catalyst 11 or aromatization catalyst 11; catalyst 12 or aromatization catalyst 12) was investigated for various ways of preparing the catalysts. The aromatization catalysts were prepared and tested as described in Examples 1 and 2. Aromatization catalyst 11 was prepared as described in Example 5. Aromatization catalyst 12 was prepared by gas-phase chlorofluorination as described in Example 1, wherein the catalyst was dried at ambient pressure prior to the chlorofluorination.

The aromatization catalysts were tested and the data are displayed in Table 3.

TABLE 3

| Catalyst | Pt wt. % | Drying Pressure | Gas-phase Halogenation | | | SOR T60 °F. | TOS hr | EOR T60 °F. | FR mF/hr |
|---|---|---|---|---|---|---|---|---|---|
| | | | Calcination Temperature °C. | Initial Temperature °C. | Final Temperature °C. | | | | |
| Reference | — | — | — | — | — | 921 | 168 | 921 | 15.5 |
| 11 | 1.00 | vacuum | 200 | 200 | 250 | 906 | 122 | 908 | 18.6 |
| 12 | 1.00 | ambient | 200 | 200 | 250 | 898 | 144 | 900 | 23.1 |

It was surprising to note that the wet impregnated Pt/KL catalyst (aromatization catalyst 12) could be dried under ambient pressure prior to the chlorofluorination without sacrificing catalyst activity.

Example 7

The properties of aromatization catalysts were investigated. More specifically, the fouling rate of aromatization catalysts (e.g., catalyst 13 or aromatization catalyst 13; catalyst 14 or aromatization catalyst 14; catalyst 15 or aromatization catalyst 15) was investigated for various ways of preparing the catalysts. The aromatization catalysts were prepared and tested as described in Examples 1 and 2. Aromatization catalyst 13, aromatization catalyst 14, and aromatization catalyst 15 were all prepared by gas-phase chlorofluorination as described in Example 1. However, various gas carriers were used during the chlorofluorination, the aromatization catalysts were tested, and the data are displayed in Table 4.

TABLE 4

| Catalyst | ex-situ Gas-phase Halogenation | | | | SOR T60 °F. | TOS [hr] | EOR T60 °F. | FR mF/hr |
|---|---|---|---|---|---|---|---|---|
| | Calcination Temperature °C. | Gas Carrier | Initial Temperature °C. | Final Temperature °C. | | | | |
| Reference | — | — | — | — | 921 | 168 | 921 | 15.5 |
| 13 | 200 | air | 200 | 250 | 909 | 121 | 909 | -1.4 |
| 14 | 200 | $N_2$ | 200 | 250 | 910 | 144 | 911 | 10.2 |
| 15 | 200 | $H_2$ | 200 | 250 | 923 | 144 | 930 | 51.9 |

Air was not used as a gas carrier due to side reactions that could damage equipment during the chlorofluorination. It was surprising to note that nitrogen as a gas carrier resulted in an aromatization catalyst (catalyst 14) with an activity similar to the reference aromatization catalyst. When hydrogen was used as a gas carrier, however, the resulting aromatization catalyst (catalyst 15) was less effective.

Example 8

The properties of aromatization catalysts were investigated. More specifically, the fouling rate of aromatization catalysts (e.g., catalyst 16 or aromatization catalyst 16; catalyst 17 or aromatization catalyst 17; catalyst 18 or aromatization catalyst 18) was investigated for various ways of preparing the catalysts. The aromatization catalysts were prepared and tested as described in Examples 1 and 2. Aromatization catalyst 16 was not subjected to a halogenation step. Aromatization catalyst 17, and aromatization catalyst 18 were both prepared by in-situ gas-phase chlorofluorination as described in Example 1, by using nitrogen as a gas carrier in the presence of ammonium chloride (AC) and ammonium fluoride (AF).

The aromatization catalysts were tested, and the data are displayed in Table 5.

TABLE 5

| | | Activation | | | Reduction | | SOR | | EOR | |
|---|---|---|---|---|---|---|---|---|---|---|
| Catalyst | Drying Gas | LHSV h$^{-1}$ | Gas | LHSV h$^{-1}$ | Gas | LHSV h$^{-1}$ | $T_{60}$ ° F. | TOS hr | $T_{60}$ ° F. | FR mF/hr |
| Reference | N$_2$ | 7200 | N/A | N/A | H$_2$ | 7200 | 893 | 168 | 899 | 24.8 |
| 16 | N$_2$ | 7200 | N/A | N/A | H$_2$ | 7200 | 921 | 144 | 998 | 603.3 |
| 17 | N$_2$ | 7200 | AC-AF-N$_2$ | AC-AF-N$_2$ | H$_2$ | 7200 | 916 | 72 | 916 | 13.2 |
| Reference | N$_2$ | 7200 | N/A | N/A | H$_2$ | 7200 | 921 | 168 | 921 | 15.5 |
| 18 | N$_2$ | 7200 | AC-AF-N$_2$ | AC-AF-N$_2$ | H$_2$ | 7200 | 925 | 144 | 927 | 4.9 |

The aromatization catalyst prepared by in-situ halogenation exhibited an activity similar to the reference aromatization catalyst.

Example 9

The properties of aromatization catalysts were investigated. More specifically, the fouling rate of aromatization catalysts (e.g., catalyst 19 or aromatization catalyst 19; catalyst 20 or aromatization catalyst 20; catalyst 21 or aromatization catalyst 21) was investigated for various ways of preparing the catalysts. The aromatization catalysts were prepared as follows. Aromatization catalyst 19 was prepared by gas-phase chlorofluorination as described in Example 1, wherein the chlorination and the fluorination were sequential. Platinum and thulium were incorporated in aromatization catalyst 20 and aromatization catalyst 21 by impregnation with an aqueous solution containing a Pt-containing compound and a Tm-containing compound. Aromatization catalyst 20 was prepared by liquid-phase chlorofluorination as described in Example 1, wherein the liquid-phase halogenation was carried out at the same time as the incorporation of platinum and thulium. Aromatization catalyst 21 was prepared by gas-phase chlorofluorination as described in Example 1, wherein the chlorofluorination was carried out subsequent to the incorporation of platinum and thulium.

The aromatization catalysts were tested, and the data are displayed in Table 6.

TABLE 6

| Catalyst | Pt wt. % | Tm wt. % | Halogen Incorporation Method | Phase | SOR $T_{60}$ ° F. | TOS hr | EOR $T_{60}$ ° F. | FR mF/hr |
|---|---|---|---|---|---|---|---|---|
| Reference | 1.0 | 0.0 | Simultaneous | Liquid | 921 | 168 | 921 | 15.5 |
| 19 | 1.0 | 0.0 | Sequential | Gas | 917 | 145 | 919 | 23.9 |
| 20 | 1.0 | 0.2 | Simultaneous | Liquid | 943 | 164 | 948 | 39.7 |
| 21 | 1.0 | 0.2 | Sequential | Gas | 907 | 144 | 911 | 32.1 |

It was surprising to note that the gas-phase halide incorporated Pt—Tm/KL catalyst (aromatization catalyst 21) significantly outperformed the Pt/KL catalyst (aromatization catalyst 19).

The present disclosure is further illustrated by the following embodiments, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first embodiment, which is a method of preparing an aromatization catalyst comprising contacting a zeolitic support with a metal-containing compound and a boron-containing compound to produce an impregnated support; and contacting the impregnated support with an activating composition to produce an aromatization catalyst, wherein the activating composition comprises a chlorine-containing compound and a fluorine-containing compound, and wherein the impregnated support is heated in the presence of the activating composition to a temperature in the range of from about 100° C. to about 500° C.

A second embodiment, which is the method of the first embodiment, wherein the impregnated support, the aromatization catalyst, or both contain non-framework boron.

A third embodiment, which is the method of any one of the first and the second embodiments, wherein the zeolitic support comprises an L-zeolite.

A fourth embodiment, which is the method of any of the first through the third embodiments, wherein the metal comprises a Group 8 transition metal.

A fifth embodiment, which is the method of any of the first through the fourth embodiments, wherein the metal-containing compound comprises platinum.

A sixth embodiment, which is the method of any of the first through the fifth embodiments, wherein the metal is present in the aromatization catalyst in an amount of from about 0.1 wt. % to about 50 wt. % by total weight of the aromatization catalyst.

A seventh embodiment, which is the method of any one of the first through the sixth embodiments, wherein the boron-containing compound is water-soluble.

An eighth embodiment, which is the method of any one of the first through the seventh embodiments, wherein the boron-containing compound is not a Brønsted acid.

A ninth embodiment, which is the method of any one of the first through the eighth embodiments, wherein the boron-containing compound is a compound characterized by at least one of formulas: $B(OR)_3$, wherein R comprises an alkyl group, a cycloalkyl, or an aryl group; $H_mB(OR)_n$, wherein R comprises an alkyl group, a cycloalkyl, or an aryl group, wherein m and n are integers from 0 to 3, and wherein the sum of m and n is 3; $B(OR')_3N$, wherein R' is a $C_1$ to $C_4$ alkyl group; or combinations thereof.

A tenth embodiment, which is the method of any one of the first through the ninth embodiments, wherein the boron-containing compound comprises triethanolamine borate, elemental boron, boric acid, boron bromide, boron carbide, boron fluoride, boron nitride, boron oxide, carborane, N,N-dimethylanilinium tetra(pentafluorophenyl)borate, methyl oxazaborolidine, nitronium tetrafluoroborate, phenylboron dichloride, phenylboron dihydroxide, potassium dodecahydrododecaborate hydrate, potassium tri-sec-butylborohydride, sodium cyanoborohydride, tetrafluoroboric acid, tri-n-amylborate, B-triboromoborazine, tri-n-butylborate, B-trichloroborazine, triethanolamineborate, triethylborate, triethylboron, trimethyoxyboroxine, trimethylborate, trimethylboron, triphenylboron, triphenylboron sodium hydroxide, tris(pentafluorophenyl)boron, tris(trimethylsiloxy)boron, triethylammonium dodecahydrododecaborate, bis (pinacolata)diboron, borane complexes, or combinations thereof.

An eleventh embodiment, which is the method of any one of the first through the tenth embodiments, wherein contacting the zeolitic support with the metal-containing compound and the boron-containing compound comprises impregnating the zeolitic support with an impregnating composition comprising the metal-containing compound and the boron-containing compound.

A twelfth embodiment, which is the method of the eleventh embodiment, wherein the boron-containing compound is present in the impregnating composition at a boron:metal atomic ratio of from about 0.5:1 to about 20:1.

A thirteenth embodiment, which is the method of any one of the eleventh and the twelfth embodiments, wherein the boron-containing compound is present in the impregnating composition at a boron:metal atomic ratio of from about 0.5:1 to about 10:1.

A fourteenth embodiment, which is the method of any one of the eleventh through the thirteenth embodiments, wherein the boron-containing compound is present in the impregnating composition at a boron:metal atomic ratio of from about 0.5:1 to about 5:1.

A fifteenth embodiment, which is the method of any one of the first through the fourteenth embodiments, wherein the chlorine-containing compound is a gas-phase chlorine-containing compound.

A sixteenth embodiment, which is the method of the fifteenth embodiment, wherein the gas-phase chlorine-containing compound comprises ammonium chloride, methyl ammonium chloride, tetramethylammonium chloride, tetraethylammonium chloride, tetrapropylammonium chloride, tetrabutylammonium chloride, methyltriethylammonium chloride, or combinations thereof.

A seventeenth embodiment, which is the method of any one of the first through the sixteenth embodiments, wherein the fluorine-containing compound is a gas-phase fluorine-containing compound.

An eighteenth embodiment, which is the method of the seventeenth embodiment, wherein the gas-phase fluorine-containing compound comprises ammonium fluoride, methyl ammonium fluoride, tetramethylammonium fluoride, tetraethylammonium fluoride, tetrapropylammonium fluoride, tetrabutylammonium fluoride, methyltriethylammonium fluoride, or combinations thereof.

A nineteenth embodiment, which is the method of any one of the first through the eighteenth embodiments, wherein the activating composition further comprises a carrier gas.

A twentieth embodiment, which is the method of the nineteenth embodiment, wherein the carrier gas comprises an inert gas, argon, helium, nitrogen, or combinations thereof.

A twenty-first embodiment, which is the method of the nineteenth embodiment, wherein the carrier gas comprises air.

A twenty-second embodiment, which is the method of the nineteenth embodiment, wherein the carrier gas comprises nitrogen and oxygen.

A twenty-third embodiment, which is the method of the nineteenth embodiment, wherein the carrier gas comprises hydrogen.

A twenty-fourth embodiment, which is the method of the nineteenth embodiment, wherein the carrier gas comprises nitrogen.

A twenty-fifth embodiment, which is the method of any one of the first through the twenty-fourth embodiments further comprising contacting the aromatization catalyst with a hydrocarbon feed under conditions suitable for the conversion of at least a portion of the hydrocarbon feed to aromatic compounds.

A twenty-sixth embodiment, which is the method of any one of the first through the twenty-fifth embodiments, wherein the impregnated support is further dried to produce a dried impregnated support prior to a step of contacting the impregnated support with an activating composition.

A twenty-seventh embodiment, which is the method of any one of the first through the twenty-sixth embodiments, wherein the impregnated support is further thermally treated to produce a thermally treated impregnated support prior to a step of contacting the impregnated support with an activating composition.

A twenty-eighth embodiment, which is a method of preparing an aromatization catalyst comprising contacting a zeolitic support with an impregnating composition comprising a platinum-containing compound and a boron-containing compound to produce a platinum-boron containing zeolitic support; and contacting the platinum-boron containing zeolitic support with an activating composition comprising a chlorine-containing compound and a fluorine-containing compound to produce an aromatization catalyst, wherein the platinum-boron containing zeolitic support is heated in the presence of the activating composition to a temperature in the range of from about 100° C. to about 500° C.

A twenty-ninth embodiment, which is the method of the twenty-eighth embodiment, wherein the zeolitic support is contacted with an impregnating composition having a boron:platinum atomic ratio of from about 0.5:1 to about 3.0:1.

A thirtieth embodiment, which is the method of any one of the twenty-eighth and the twenty-ninth embodiments, wherein the boron-containing compound comprises triethanolamine borate, elemental boron, boric acid, boron bromide, boron carbide, boron fluoride, boron nitride, boron oxide, carborane, N,N-dimethylanilinium tetra(pentafluorophenyl)borate, methyl oxazaborolidine, nitronium tetrafluoroborate, phenylboron dichloride, phenylboron dihydroxide, potassium dodecahydrododecaborate hydrate, potassium tri-sec-butylborohydride, sodium cyanoborohydride, tetrafluoroboric acid, tri-n-amylborate, B-triboromoborazine, tri-n-butylborate, B-trichloroborazine, triethanolamineborate, triethylborate, triethylboron, trimethyoxyboroxine, trimethylborate, trimethylboron, triphenylboron, triphenylboron sodium hydroxide, tris(pentafluorophenyl)boron, tris(trimethylsiloxy)boron, triethylammonium dodecahydrododecaborate, bis(pinacolata)diboron, borane complexes, or combinations thereof.

A thirty-first embodiment, which is the method of any one of the twenty-eighth through the thirtieth embodiments further comprising contacting the aromatization catalyst with a hydrocarbon feed under conditions suitable for the conversion of at least a portion of the hydrocarbon feed to aromatic compounds, wherein the aromatization catalyst has a reduced cracking tendency when compared to the cracking tendency of a similar aromatization catalyst lacking non-framework boron, wherein the reduced cracking tendency is represented by an increased wt. % of C5+ products, based on the total weight of the products, and wherein the wt. % of C5+ products for the aromatization catalyst is increased by at least about 2 wt. %, when compared to a similar aromatization catalyst lacking non-framework boron.

A thirty-second embodiment, which is a catalyst composition comprising a zeolitic support, chlorine, fluorine, platinum and non-framework boron; wherein the zeolitic support further comprises an L-zeolite.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of preparing an aromatization catalyst comprising:
contacting a zeolitic support with a metal-containing compound and a boron-containing compound to produce an impregnated support; and
contacting the impregnated support with an activating composition to produce an aromatization catalyst, wherein the activating composition comprises a chlorine-containing compound and a fluorine-containing compound, and wherein the impregnated support is heated in the presence of the activating composition to a temperature in the range of from about 100° C. to about 500° C.

2. The method of claim 1 wherein the impregnated support, the aromatization catalyst, or both contain non-framework boron.

3. The method of claim 1 wherein the zeolitic support comprises an L-zeolite.

4. The method of claim 1 wherein the metal comprises a Group 8 transition metal.

5. The method of claim 1 wherein the metal-containing compound comprises platinum.

6. The method of claim 1 wherein the metal is present in the aromatization catalyst in an amount of from about 0.1 wt. % to about 50 wt. % by total weight of the aromatization catalyst.

7. The method of claim 1 wherein the boron-containing compound is water-soluble.

8. The method of claim 1 wherein the boron-containing compound is not a Brønsted acid.

9. The method of claim 1 wherein the boron-containing compound is a compound characterized by at least one of formulas: $B(OR)_3$, wherein R comprises an alkyl group, a cycloalkyl, or an aryl group; $H_mB(OR)_n$, wherein R comprises an alkyl group, a cycloalkyl, or an aryl group, wherein m and n are integers from 0 to 3, and wherein the sum of m and n is 3; $B(OR')_3N$, wherein R' is a $C_1$ to $C_4$ alkyl group; or combinations thereof.

10. The method of claim 1 wherein the boron-containing compound comprises triethanolamine borate, elemental boron, boric acid, boron bromide, boron carbide, boron fluoride, boron nitride, boron oxide, carborane, N,N-dimethylanilinium tetra(pentafluorophenyl)borate, methyl oxazaborolidine, nitronium tetrafluoroborate, phenylboron dichloride, phenylboron dihydroxide, potassium dodecahydrododecaborate hydrate, potassium tri-sec-butylborohydride, sodium cyanoborohydride, tetrafluoroboric acid, tri-n-amylborate, B-triboromoborazine, tri-n-butylborate, B-trichloroborazine, triethanolamineborate, triethylborate, triethylboron, trimethyoxyboroxine, trimethylborate, trimethylboron, triphenylboron, triphenylboron sodium hydroxide, tris(pentafluorophenyl)boron, tris(trimethylsiloxy)boron, triethylammonium dodecahydrododecaborate, bis(pinacolata)diboron, borane complexes, or combinations thereof.

11. The method of claim 1 wherein contacting the zeolitic support with the metal-containing compound and the boron-containing compound comprises impregnating the zeolitic support with an impregnating composition comprising the metal-containing compound and the boron-containing compound.

12. The method of claim 11 wherein the boron-containing compound is present in the impregnating composition at a boron:metal atomic ratio of from about 0.5:1 to about 20:1.

13. The method of claim 1 wherein the chlorine-containing compound is a gas-phase chlorine-containing compound.

14. The method of claim 13 wherein the gas-phase chlorine-containing compound comprises ammonium chloride, methyl ammonium chloride, tetramethylammonium chloride, tetraethylammonium chloride, tetrapropylammonium chloride, tetrabutylammonium chloride, methyltriethylammonium chloride, or combinations thereof.

15. The method of claim 1 wherein the fluorine-containing compound is a gas-phase fluorine-containing compound.

16. The method of claim 15 wherein the gas-phase fluorine-containing compound comprises
ammonium fluoride, methyl ammonium fluoride, tetramethylammonium fluoride, tetraethylammonium fluoride, tetrapropylammonium fluoride, tetrabutylammonium fluoride, methyltriethylammonium fluoride, or combinations thereof.

17. The method of claim 1 wherein the activating composition further comprises a carrier gas.

18. The method of claim 1 wherein the impregnated support is further thermally treated to produce a thermally treated impregnated support prior to a step of contacting the impregnated support with an activating composition.

19. A method of preparing an aromatization catalyst comprising:
contacting a zeolitic support with an impregnating composition comprising a platinum-containing compound and a boron-containing compound to produce a platinum-boron containing zeolitic support; and
contacting the platinum-boron containing zeolitic support with an activating composition comprising a chlorine-containing compound and a fluorine-containing compound to produce an aromatization catalyst, wherein the platinum-boron containing zeolitic support is heated in the presence of the activating composition to a temperature in the range of from about 100° C. to about 500° C.

20. The method of claim 19 wherein the zeolitic support is contacted with an impregnating composition having a boron:platinum atomic ratio of from about 0.5:1 to about 3.0:1.

* * * * *